US008246959B1

(12) United States Patent (10) Patent No.: US 8,246,959 B1
Clark et al. (45) Date of Patent: Aug. 21, 2012

(54) DENDRITIC CELL-ASSOCIATED LECTIN-LIKE MOLECULES, COMPOSITIONS AND METHODS OF USE

(75) Inventors: Edward A. Clark, Seattle, WA (US); Elizabeth Ryan, Cappawhite (IE); Aaron Marshall, Winnipeg (CA); Kevin Draves, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/620,582

(22) Filed: Jan. 5, 2007

Related U.S. Application Data

(62) Division of application No. 10/903,887, filed on Jul. 30, 2004, now abandoned.

(60) Provisional application No. 60/491,826, filed on Aug. 1, 2003.

(51) Int. Cl.
*A61K 39/395* (2006.01)
*A61K 39/00* (2006.01)

(52) U.S. Cl. .................................. 424/173.1; 424/178.1

(58) Field of Classification Search ......................... None
See application file for complete search history.

(56) References Cited

U.S. PATENT DOCUMENTS

| 6,497,876 | B1 | 12/2002 | Maraskovsky et al. | |
|---|---|---|---|---|
| 2002/0164312 | A1 | 11/2002 | Schultes et al. | |
| 2002/0187131 | A1* | 12/2002 | Hawiger et al. ............... | 424/93.7 |
| 2003/0032050 | A1 | 2/2003 | Berzofsky et al. | |
| 2004/0005592 | A1* | 1/2004 | Emtage et al. .................... | 435/6 |

FOREIGN PATENT DOCUMENTS

| WO | 02/070539 A2 | 9/2002 |
|---|---|---|
| WO | WO 03/031578 * | 4/2003 |

OTHER PUBLICATIONS

Janeway and Travers, 1997, Immunobiology, pp. 3:3-3:4.*
Genbank Accession No. BG213959, submitted by Harrington, J.J., et al., *Nat Biotech* 19(5)440-445 (2001). Initially released on Apr. 21, 2001. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. AI719511, submitted by Hillier, L., et al., unpublished. Initially release on Jun. 10, 1999. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. AW237307, submitted by Strausberg on behalf of NCI-CGAP, unpublished. Initially released on Dec. 13, 1999. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. AI879793, submitted by Hillier, L., et al., unpublished. Initially released on Jul. 21, 1999. Discloses the nucleic acid sequence of a truncated *homo sapiens* cDNA fragment that includes a portion of the nucleic acid sequence coding DCAL-1, set forth in the present application as SEQ ID No. 1.
Genbank Accession No. BG195772, submitted by Harrington, J.J., et al., *Nat. Biotech* 19(5):440-445 (2001). Initially released on Apr. 21, 2001. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. BG258759, submitted by Strausberg on behalf of NCI-CGAP, unpublished. Initially released on Feb. 12, 2001. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. AA746003, submitted by Strausberg on behalf of NCI-CGAP, unpublished. Initially released on Jan. 16, 1998. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. BG391322, submitted by Strausberg on behalf of NCI-CGAP, unpublished. Initially released on Mar. 5, 2001. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. BG391235, submitted by Strausberg on behalf of NCI-CGAP, unpublished. Initially released on Mar. 5, 2001. Discloses the nucleic acid sequence of a truncated *homo sapiens* cDNA fragment that includes a portion of the nucleic acid sequence encoding DCAL-1, set forth in the present application as SEQ ID No. 1.
Genbank Accession No. AI271437, submitted by Strausberg on behalf of NCI-CGAP, unpublished. Initially released on Nov. 17, 1998. Discloses the nucleic acid sequence of a truncated *homo sapiens* cDNA fragment that includes a portion of the nucleic acid sequence encoding DCAL-1, set forth in the present application as SEQ ID No. 1.

(Continued)

*Primary Examiner* — Amy Juedes
(74) *Attorney, Agent, or Firm* — Christensen O'Connor Johnson Kindness PLLC

(57) ABSTRACT

The invention provides novel dendritic cell-associated lectin-like (DCAL-1) molecules, compositions and therapeutic methods of use. In one aspect, the invention provides isolated nucleic acid molecules that are capable of remaining hybridized to SEQ ID NO:1 or SEQ ID NO:3, including nucleic acid molecules that encode DCAL-1 polypeptides. In another aspect, the invention provides DCAL-1 polypeptides and portions thereof which are useful to stimulate T cell proliferation. In another aspect, the invention provides antibodies that specifically bind to DCAL-1 which are useful for promoting maturation of dendritic cells and for stimulating an immune response in vivo. In another aspect the invention provides methods of stimulating an immune response in an animal comprising introducing into the animal an anti-DCAL-1 antibody of the invention.

13 Claims, 8 Drawing Sheets

OTHER PUBLICATIONS

Aicher, A., et al., "Differential Role for p38 Mitogen-Activated Protein Kinase in Regulating CD40-Induced Gene Expression in Dendritic Cells and B Cells," *The Journal of Immunology* 163:5786-5795, 1999.

Aicher, A., et al., "Characterization of Human Inducible Costimulator Ligand Expression and Function," *The Journal of Immunology* 164:4689-4696, 2000.

Banchereau, J., et al., "Immunobiology of Dendritic Cells," *Annual Review Immunology* 18:767-811, 2000.

Geijtenbeek, T., et al., "Identification of DC-SIGN, a Novel Dendritic Cell-Specific ICAM-3 Receptor That Supports Primary Immune Responses," *Cell* 100: 575-585, Mar. 3, 2000.

Hawiger, D., et al., "Dendritic Cells Induce Peripheral T Cell Unresponsiveness Under Steady Stated Conditions In Vivo," *J. Exp. Med.* 194(6):769-779, Sep. 17, 2001.

Mahnke, K., et al., "The Dendritic Cell Receptor for Endocytosis, DEC-205, Can Recycle and Enhance Antigen Presentation Via Major Histocompatibility Complex Class II-Positive Lysosomal Compartments," *The Journal of Cell Biology* 151(3):673-683, Oct. 30, 2000.

Marshall, A.J., "A Novel B Lymphocyte-Associated Adaptor Protein, Bam32, Regulates Antigen Receptor Signaling Downstream of Phosphatidylinositol 3-Kinase," *J. Exp. Med.* 191(8):1319-1331, Apr. 17, 2000.

Palucka, K., and J. Banchereau, "How Dendritic Cells and Microbes Interact to Elicit or Subvert Protective Immune Responses," *Current Opinion. in Immunology* 14:420-431, 2002.

Rescigno, M., "Dendritic Cells and the Complexity of Microbial Infection," *Trends in Microbiology* 10(9):425-431, Sep. 2002.

Ryan, E.J., et al., "Dendritic Cell-Associated Lectin-1: A Novel Dendritic Cell-Associated, C-Type Lectin-Like Molecule Enhances T Cell Secretion of IL-4," *The Journal of Immunology* 169:5638-5648, 2002.

Bluestone, J.A., and A.K. Abbas, "Natural Versus Adaptive Regulatory T Cells," Nature Reviews Immunology 3(3):253-257, Mar. 2003.

Banchereau, J., and R.M. Steinman, "Dendritic Cells and the Control of Immunity," Nature 392(6673):245-252, Mar. 1998.

Diehl, S., and M. Rincón, "The Two Faces of IL-6 on Th1/Th2 Differentiation," Molecular Immunology 39(9):531-536, Dec. 2002.

Dubois, B., et al., "Critical Role of IL-12 in Dendritic Cell-Induced Differentiation of Naive B Lymphocytes," Journal of Immunology 161(5):2223-2231, Sep. 1998.

Lu, H.-T., et al., "Defective IL-12 Production in Mitogen-Activated Protein (MAP) Kinase Kinase 3 (Mkk3)-Deficient Mice," EMBO Journal 18(7):1845-1857, Apr. 1999.

Ni, K., and H.C. O'Neill, "The Role of Dendritic Cells in T Cell Activation," Immunology and Cell Biology 75(3):223-230, Jun. 1997.

Skok, J., et al., "Dendritic Cell-Derived IL-12 Promotes B Cell Induction of Th2 Differentiation: A Feedback Regulation of Th1 Development," Journal of Immunology 163(8):4284-4291, Oct. 1999.

Koch, F., et al., "High Level IL-12 Production by Murine Dendritic Cells: Upregulation via MHC Class II and CD40 Molecules and Downregulation by IL-4 and IL-10," Journal of Experimental Medicine 184(2):741-746, Aug. 1996.

Ruedl, C., and S. Hubele, "Maturation of Peyer's Patch Dendritic Cells in vitro Upon Stimulation via Cytokines or CD40 Triggering," European Journal of Immunology 27(6):1325-1330, Jun. 1997.

Ferlin, W.G., "The Induction of a Protective Response in Leishmania Major-Infected BALB/c Mice With Anti-CD40 mAb," European Journal of Immunology 28(2):525-531, Feb. 1998.

Turner, J.G., et al., "Anti-CD40 Antibody Induces Antitumor and Antimetastatic Effects: The Role of NK Cells," Journal of Immunology 166(1):89-94, Jan. 2001.

Demangel, C., et al., "Stimulation of Dendritic Cells via CD40 Enhances Immune Responses to Mycobacterium Tuberculosis Infection," Infection and Immunity 69(4):2456-2461, Apr. 2001.

Hawiger, D., et al., "Dendritic Cells Induce Peripheral T Cell Unresponsiveness Under Steady State Conditions In Vivo," Journal of Experimental Medicine 194(6):769-779, Sep. 2001.

\* cited by examiner

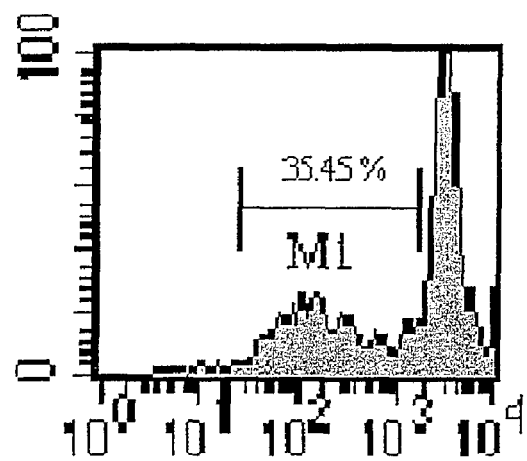
*Fig. 4A.* Anti-CD3 0.1 μg/ml
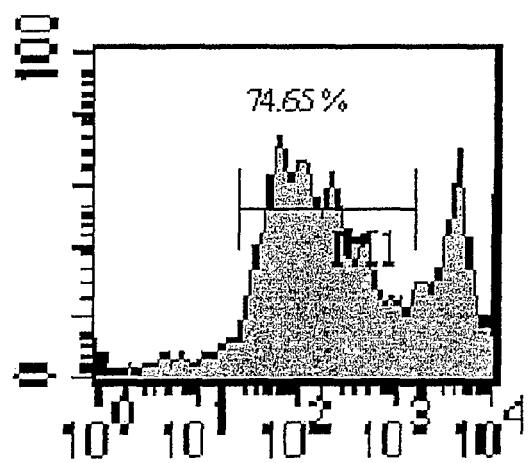
*Fig. 4B.* Anti-CD3 0.1 μg/ml + DCAL-1 10 μg/ml
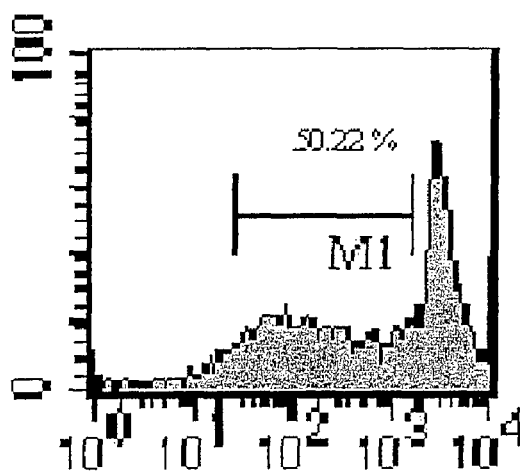
*Fig. 4C.* Anti-CD3 0.1 μg/ml + DC-SIGN 10 μg/ml FIG 5A    FIG 5B
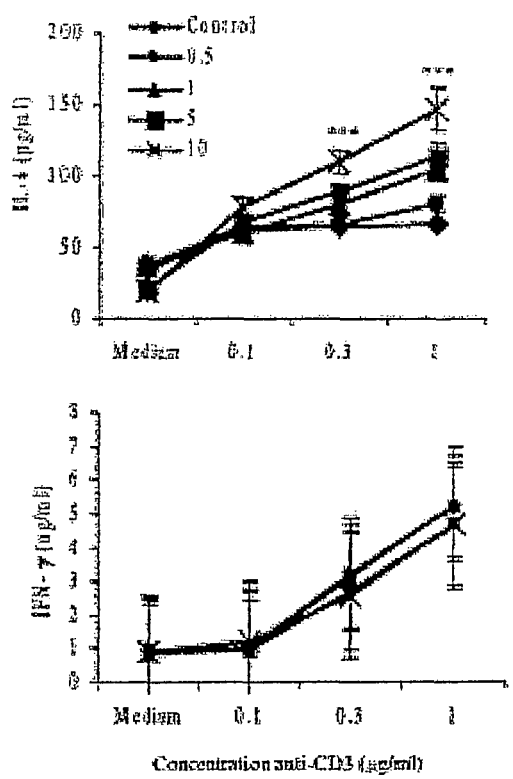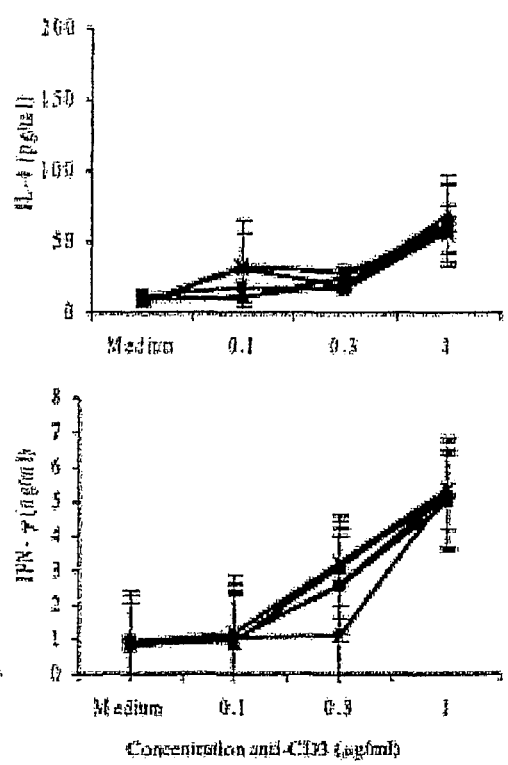
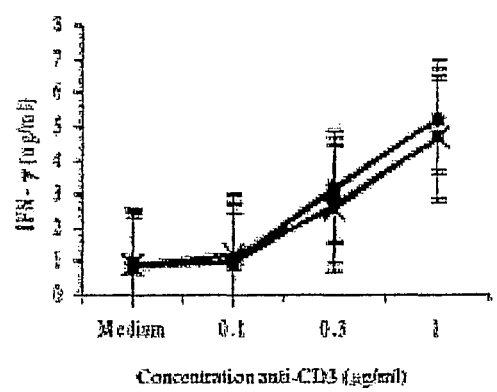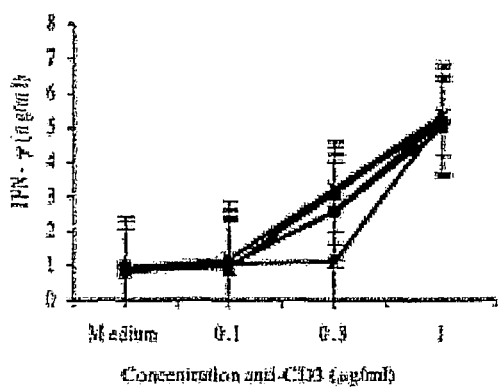
FIG 5C    FIG 5D

DENDRITIC CELL-ASSOCIATED LECTIN-LIKE MOLECULES, COMPOSITIONS AND METHODS OF USE

CROSS-REFERENCE TO RELATED APPLICATION

This application is a divisional of U.S. patent application Ser. No. 10/903,887, filed Jul. 30, 2004, which claims the benefit of U.S. Application No. 60/491,826, filed Aug. 1, 2003.

GOVERNMENT RIGHTS

This invention was funded, in part, by The National Institutes of Health Grant Numbers RR00166, GM37905, and AI44257. The United States government has certain rights in this invention.

FIELD OF THE INVENTION

The present invention relates to novel cell surface molecules which can be used to modulate T cell activation and dendritic cell maturation for therapeutic purposes.

BACKGROUND OF THE INVENTION

Dendritic cells (DCs) play a key role in the immune system, for they are the most effective antigen presenting cells for initiating primary immune responses and they have the ability to initiate T cell mediated immune responses. DCs have widespread tissue distribution and are generally present in the body at locations that are routinely exposed to foreign antigens, such as the skin, lung, gut, blood and lymphoid tissues (see Steinman, R. M., *Annu. Rev. Immunol.* 9:271-2996 (1991)).

Generally, DCs are either classified as immature or mature. Peripherally located immature DCs endocytose and process antigen efficiently, but express low levels of costimulatory molecules CD40, CD80 and CD86 (see Banchereau et al., *Nature* 392:245 (1998)). During the maturation process, DCs migrate to the T lymphocyte areas of draining lymph nodes. After exposure to inflammatory stimuli, DCs mature, lose their antigen processing capacity, display increased levels of costimulatory molecules and secrete increased amounts of cytokines and chemokines that aid T cell activation. In addition to their role in inducing immunity to foreign antigens, DCs are involved in inducing tolerance to self-antigens. Recent studies have shown a correlation between the presence of DCs with a semi-mature DC phenotype and the ability to tolerize lymph node T cells against tissue-derived self-antigens. Lutz, M. B., et al., *Trends Immunol.* 23 (9):445-449 (2002); Steinman R. M. et al., *Annu. Rev. Immunol.* 21:685-711 (2003).

DCs express surface receptors that recognize pathogen-associated molecule patterns, such as bacterial LPS, unmethylated CpG motifs of bacterial DNA, and double-stranded viral RNA (see Underhill, D., et al., *Curr. Opin. Immunol.* 14:103 (2002)). Antigen receptors expressed by DCs include members of the C-type lectin family, which bind sugars in a calcium-dependent manner using highly conserved carbohydrate recognition domains (CRDs). Recently, C-type lectin-like receptors have been characterized which consist of a CRD-like domain that may bind protein or lipids rather than carbohydrates (Kogelberg, H., et al., *Curr. Opin. Struct. Biol.* 11:635 (2001); Cambi A. et al., *Curr. Opin. Cell Biol.* 15(5): 539-546 (2003)).

Given the important role DCs play in immune regulation, there is a need for agents that modulate the ability of DCs to stimulate the immune response. It has now been discovered that a novel dendritic cell-associated C-type Lectin-like molecule (DCAL-1) type II acts as a costimulatory molecule to enhance IL-4 production by CD4+ T cells and also plays a role in DC maturation.

SUMMARY OF THE INVENTION

In accordance with the foregoing, in one aspect the present invention provides isolated nucleic acid molecules capable of remaining hybridized to the nucleic acid molecules of SEQ ID NO:1 or SEQ ID NO:3 or to their antisense complements under stringent wash conditions. In some embodiments, the invention provides isolated nucleic acid molecules encoding human dendritic cell-associated, C-type lectin-like (DCAL-1) polypeptides comprising the amino acid sequences provided herein as SEQ ID NO:2 or SEQ ID NO:4, or portions thereof. In other embodiments the invention provides isolated nucleic acid molecules comprising SEQ ID NO:1 or SEQ ID NO:3, or nucleic acid molecules substantially similar thereto. In further embodiments, expression vectors comprising a nucleic acid molecule of the invention operably linked to a promoter are provided. In other embodiments, host cells are provided comprising an expression vector of the invention.

In another aspect, the invention provides isolated DCAL-1 polypeptides and portions or modifications thereof having the biological activity of the polypeptides represented by SEQ ID NO:2 or SEQ ID NO:4. In some embodiments, the DCAL-1 polypeptides further comprise an affinity tag. In some embodiments, the invention provides methods of making DCAL-1 polypeptides. In some embodiments, the invention provides DCAL-1 soluble receptor polypeptides. In some embodiments, the invention provides pharmaceutical compositions comprising DCAL-1 polypeptides.

In another aspect, the invention provides antibodies or fragments thereof that specifically bind to the DCAL-1 polypeptides of the invention. In some embodiments, the anti-DCAL-1 antibodies or fragments thereof are conjugated to a moiety such as an imaging moiety, a cytotoxic moiety, or an antigenic peptide.

In another aspect, the invention provides methods for stimulating an immune response in an animal, comprising introducing into the animal an anti-DCAL antibody, in an amount sufficient to stimulate an immune response in the animal. In some embodiments, the anti-DCAL-1 antibody is conjugated to an antigenic peptide.

In another aspect, the invention provides methods for promoting maturation of immature dendritic cells in vitro comprising contacting immature dendritic cells in cell culture with an amount of an anti-DCAL-1 antibody sufficient to promote dendritic cell maturation in at least a portion of the cultured cells.

In another aspect, the invention provides a method of stimulating the proliferation of CD4+ T cells in vitro, comprising the steps of contacting the CD4+ T cells with CD3+, and contacting said CD3+ stimulated T cells with a DCAL-1 soluble receptor polypeptide.

In yet another aspect, the invention provides a method of inhibiting an immune response in an animal, comprising introducing a DCAL-1 soluble receptor into an animal in an amount sufficient to inhibit an immune response in the animal.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4A demonstrates the percentage of proliferating of CD4+ T cells (35.45%) in the presence of CD3 mAb (0.3 ug/ml);

FIG. 4B demonstrates enhanced proliferation of CD4+ T cells (74.65%) in the presence of CD3 mAb (0.3 ug/ml) and the DCAL-1 soluble receptor (10 ug/ml);

FIG. 4C demonstrates that the control DC-SIGN fusion protein does not enhance proliferation in CD3 mAb stimulated cells to the same level as the DCAL-1 soluble receptor;

FIG. 5A graphically illustrates that the DCAL-1 soluble receptor enhances anti-CD3 induced IL-4 production by CD45RA+ T cells in a dose dependant manner;

FIG. 5B graphically illustrates that the control DC-SIGN fusion protein does not affect the secretion of IL-4 in anti-CD3 induced CD45RA+ T cells;

FIG. 5C graphically illustrates that the DCAL-1 soluble receptor does not inhibit IFN-γ secretion in anti-CD3 stimulated CD45RA+ T cells;

FIG. 5D graphically illustrates that the control DC-SIGN fusion protein does not inhibit IFN-γ secretion in anti-CD3 stimulated CD45RA+ T cells;

DETAILED DESCRIPTION OF THE PREFERRED EMBODIMENT

Figure 1:
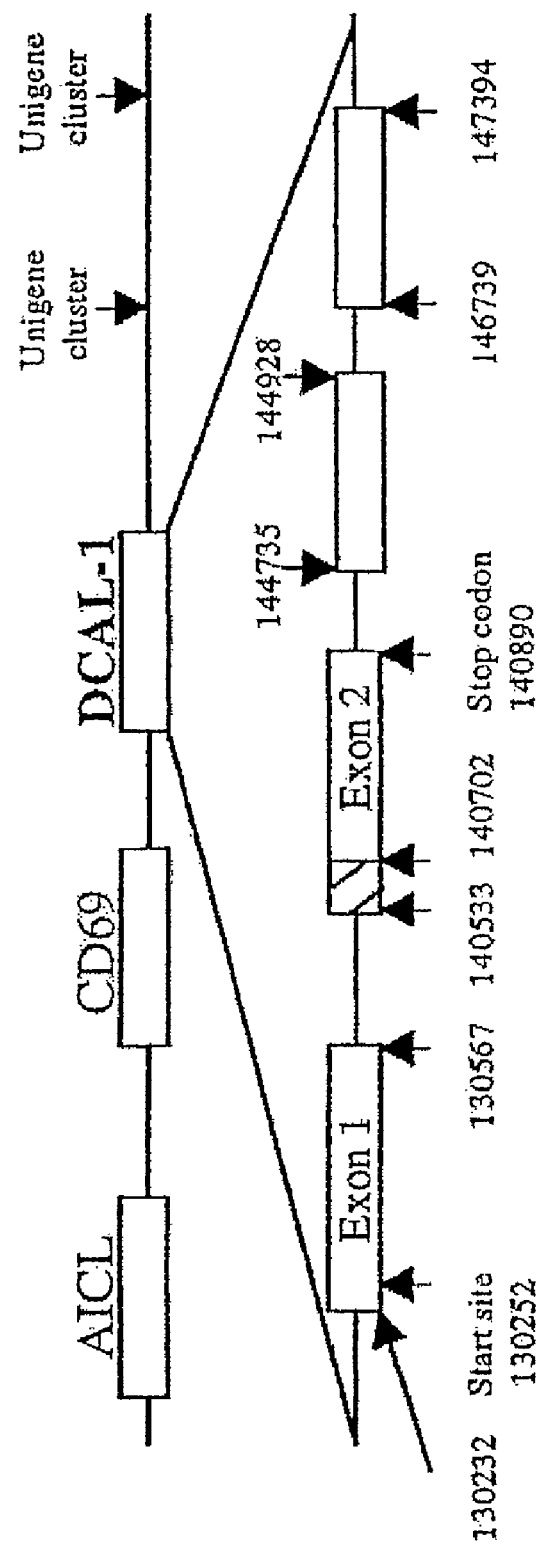
FIG. 1 illustrates that the DCAL-1 chromosomal locus is within a cluster of C-type lectin-like loci on human chromosome 12p12-13 just 3' to the CD69 locus. A schematic diagram showing the DCAL-1 gene structure is also provided.

Unless specifically defined herein, all terms used herein have the same meaning as they would to one skilled in the art of the present invention. Practitioners are particularly directed to Sambrook, et al., *Molecular Cloning: A Laboratory Manual*, 2$^{nd}$ ed., Cold Spring Harbor Press, Plainsview, New York (1989), and Ausubel, et al., *Current Protocols in Molecular Biology* (Supplement 47), John Wiley & Sons, New York (1999), for definitions and terms of the art.

The following definitions are provided in order to provide clarity with respect to the terms as they are used in the specification and claims to describe the present invention.

As used herein, the term "nucleic acid molecule" encompasses both deoxyribonucleotides and ribonucleotides and refers to a polymeric form of nucleotides including two or more nucleotide monomers. The nucleotides can be naturally occurring, artificial and/or modified nucleotides. Examples of nucleic acid molecules include oligonucleotides which typically have a length of from 2 nucleotides to about 100 nucleotides, and polynucleotides, which typically have a length greater than about 100 nucleotides.

As used within the context of the present invention, "substantially similar" nucleic acid sequences encompass allelic variants and genetically engineered or synthetic variants of the DCAL-1 gene that contain conservative amino acid substitutions and/or minor additions, substitutions or deletions of amino acids. Nucleic acid sequence variants also encompass degeneracies in the DNA code.

As used herein, the term "isolated" means that the material, such as a nucleic acid molecule or a polypeptide, is removed from its natural environment. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "stringent wash conditions" refers to the conditions used to wash a nucleic acid blot, such as a Southern blot. In general, stringent wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Numerous equations for calculating Tm are known in the art, and are specific for DNA, RNA and DNA-RNA hybrids and polynucleotide probe sequences of varying length (see, for example, Sambrook, et al., *Molecular Cloning: A Laboratory Manual*, Second Edition (Cold Spring Harbor Press 1989); Ausubel, et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating Tm based on user defined criteria. Such programs can also analyze a given sequence under defined conditions and identify suitable probe sequences. Typically, hybridization of longer polynucleotide sequences (e.g., >50 base pairs) is performed at temperatures of about 20-25° C. below the calculated Tm. For smaller probes (e.g., <50 base pairs) hybridization is typically carried out at the Tm or 5-10° C. below. This allows for the maximum rate of hybridization for DNA-DNA and DNA-RNA hybrids. Higher degrees of stringency at lower temperatures can be achieved with the addition of formamide which reduces the Tm of the hybrid about 1° C. for each 1% formamide in the buffer solution. Suitable stringent hybridization conditions are equivalent to about a 5 hours to overnight incubation at about 42° C. in a solution comprising: about 40-50% formamide, up to about 6×SSC, about 5×Denhardt's solution, zero up to about 10% dextran sulfate, and about 10-20 µg/ml denatured commercially-available carrier DNA. Generally, such stringent conditions include temperatures of 20-70° C. and a hybridization buffer containing up to 6×SSC and 0-50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

The following are representative hybridization and stringent wash conditions useful for identifying (by Southern blotting) nucleic acid molecules of the invention that are capable of hybridizing to a nucleic acid molecule selected from the group consisting of SEQ ID NOS:1 and 3 or to the antisense complement of a nucleic acid molecule selected from the group consisting of SEQ ID NOS:1 and 3: hybridization in 6×SSC, 5 X Denhardt's, 0.5% SDS at 55-58° C. for 12 hours, followed by washing in 2×SSC, 0.5% SDS at 55-58° C. for 30 minutes. An optional further wash can be conducted in 1×SSC, 0.5% SDS at 55-58° C. for 30 minutes, followed by an additional, optional wash in 0.5×SSC, 0.5% SDS at 55-58° C. for 30 minutes.

As used herein, the terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

As used herein, the term "expression vector" is used to denote a DNA molecule, linear or circular, that comprises a segment encoding a polypeptide of the invention operably linked to additional segments that provide for its transcription. Such additional segments include promoter and terminator sequences, and may also include one or more origins of replication, one or more selectable markers, an enhancer, a polyadenylation signal, etc. As used herein, the term "operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained. As used herein, the term "host cell", may be a prokaryotic or a eukaryotic cell. Typical prokaryotic host cells include various strains of E. coli. Typical eukaryotic host cells include yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

As used herein, the term "soluble receptor" is a receptor polypeptide that is not bound to a cell membrane. Soluble receptors are most commonly ligand-binding receptor polypeptides that lack transmembrane and cytoplasmic domains.

The term "affinity tag" is used herein to denote a polypeptide segment that can be attached to a second polypeptide to provide for purification or provide sites for attachment of the second polypeptide to a substrate.

As used herein, the term "antibody" encompasses polyclonal and monoclonal antibody preparations, complement determining region-grafted antibody preparations, as well as preparations including hybrid antibodies, altered antibodies, F(ab)'$_2$ fragments, Fab molecules, Fv fragments, single domain antibodies, chimeric antibodies and functional fragments thereof which exhibit immunological binding properties of the parent antibody molecule. The antibodies may be derived, for example, from mouse, hamster or human genes. The antibodies of the invention may be humanized. The antibodies of the invention may be an intact molecule, a fragment thereof (such as scFv, Fv, Fd, Fab, Fab', F(ab)'$_2$ fragments, light chain variable region ($V_L$), heavy chain variable region ($V_H$) and combinations thereof), or multimers or aggregates of intact molecules and/or fragments. The antibodies and fragments thereof may occur in nature or be produced, e.g., by immunization, synthesis; or through genetic engineering.

As used herein, a "tumor associated antigen" is an antigen in a living body that is made by tumor cells, and which may be presented on the tumor surface, or circulating or both.

As used herein, the term "dendritic cell" refers to a bone-marrow derived cell that can internalize antigen and process the antigen, such that the antigen, or peptide derived from the antigen, is presented in the context of both the MHC class I complex and the MHC class II complexes. A DC of the invention typically has the phenotype and characteristics of the DCs described in Steinman, et al., Annual Rev. Immunol. 9:271-296 (1991). Dendritic cells include both immunogenic and tolerogenic antigen presenting cells, and may be classified as immature, semi-mature or fully mature.

As used herein, the term "immature dendritic cells" refers to dendritic cells that lack the cell surface markers found on mature DCs, such as dendritic cells lacking CD83, and lacking CD14; express low levels of CCR7 and usually low levels of the costimulatory molecules CD40, CD80 and CD86. Immature DCs usually express CD1a and CCR1, CCR2, CCR5 and CXCR1.

As used herein, the term "mature dendritic cells" refers to DCs that have increased expression of MHC class 11, CD40, CD80, CD83 and CD86; are characterized by their release of proinflammatory cytokines, and their ability to cause increased proliferation of naïve allogeneic T cells and/or increased production of DC cytokines in a mixed lymphocyte reaction. Mature DCs typically express high levels of CCR7, and CXCR4 and low levels of CCR1 and CCR5.

As used herein, the term "semi-mature dendritic cells" refers to DCs that have lost some of the characteristics of immature DCs but do not have all the characteristics of a mature DC phenotype and are characterized by their ability to induce a tolerogenic immune response to self-antigens.

As used herein, the term "promoting dendritic cell maturation" refers to a stimuli which upon exposure to immature dendritic cells results in a semi-mature or mature dendritic cell phenotype in a portion of the exposed cells.

In accordance with one aspect of the present invention, nucleic acid molecules encoding dendritic cell-associated lectin-1 (DCAL-1) were unexpectedly identified during a screen for genes expressed in human germinal centers in a cDNA library derived from tonsillar cells enriched for follicular dendritic cells (see Clark, et al., J. Exp. Med. 191:1319, incorporated herein by reference in its entirety). Analysis of the isolated nucleic acid molecules revealed a clone that encodes a previously unknown C-type lectin designated DCAL-1 (dendritic cell associated lectin-1) shown as SEQ ID NO:2, encoded by SEQ ID NO:1. The full length sequence was obtained using 5' and 3' RACE PCR, and full-length DCAL-1 was cloned from human tonsillar B cells as described in Example 1. The gene structure of DCAL-1 was determined by sequence analysis and EST mapping, as further described in Example 1. Analysis of SEQ ID NO:1 revealed an open reading frame encoding 223 amino acids (SEQ ID NO:2) comprising features typical of a type II C-type lectin including an intracellular domain, a transmembrane domain, and an extracellular domain containing a single CRD-like domain. In addition, a shorter splice variant of DCAL-1 was identified, provided as SEQ ID NO:3, encoding SEQ ID NO:4. The difference between the splice variants is that the long form of the DCAL-1 protein (SEQ ID NO:2) contains a stalk region (peptides 106-161) separating the CRD from the transmembrane region, whereas the short form of DCAL-1 (SEQ ID NO:4) does not have a stalk region. As shown in FIG. 1 and further described in Example 1, the DCAL-1 locus is within a cluster of C-type lectin loci on human chromosome 12p12-13, just 3' to the CD69 locus.

In one aspect, the present invention provides isolated nucleic acid molecules that are capable of remaining hybridized to the nucleic acid molecules of SEQ ID NO:1 or SEQ ID NO:3, or to their antisense complements, under stringent wash conditions. The isolated nucleic acid molecules of the present invention are provided free from some or all of other genes with which they are naturally associated and may include naturally occurring 5' and 3' untranslated sequences that represent regulatory regions such as promoters and terminators. The identification of regulatory regions within the naturally occurring 5' and 3' untranslated regions will be evident to one of ordinary skill in the art (for review, see Dynan and Tijan, *Nature* 316:774-778, 1985).

The isolated nucleic acid molecules of the present invention can be isolated from a variety of species such as, for example, murine, porcine, bovine, canine, feline, equine and other primates. DNA molecules of this aspect of the invention can be isolated using SEQ ID NO:1 or 3, or a portion thereof, as a probe to directly detect DCAL-1 sequences in cells. Such DNA probes are generally synthetic oligonucleotides, but may also be generated from cloned cDNA or genomic sequences and will generally comprise at least 12 nucleotides, more often about 14 nucleotides to about 25 or more nucleotides, sometimes 40 to 60 nucleotides and in some instances a substantial portion or even the entire DCAL-1 gene or cDNA. The isolated nucleic acid molecules include, for example, genomic DNA sequences, cDNA sequences, RNA sequences and synthetic oligonucleotides. Typically, the synthetic oligonucleotides of the present invention have at least 85% identity to a corresponding portion of a DCAL-1 sequence (SEQ ID NO:1 or 3, or its complement).

The present invention further relates to isolated nucleic acid molecules that hybridize under stringent wash conditions to the herein described sequences if there is at least 70%, preferably at least 90%, and more preferably at least 95% identity between the sequences. In addition, substantially similar DNA sequences are those that are capable of hybridizing to the DNA sequences of the present invention under stringent wash conditions.

In one embodiment, the present invention provides isolated nucleic acid molecules encoding human dendritic cell-associated, C-type lectin-like (DCAL-1) polypeptides comprising amino acid sequences described herein as SEQ ID NO:2 or SEQ ID NO:4 or portions thereof. The polypeptides of the present invention may be encoded by nucleic acid molecules that contain nucleic sequences that are substantially similar to the nucleic acid sequences disclosed herein. Those of skill in the art will recognize that the degeneracy of the genetic code allows for a plurality of polynucleotides to encode to the identical amino acid sequence. In addition, isolated nucleic acid molecules may encode polypeptides having minor modifications to the polypeptides of SEQ ID NO:2 or SEQ ID NO:4 that retain the primary biological activity of DCAL-1, as described herein.

In another embodiment, this aspect of the invention provides nucleic acid molecules comprising SEQ ID NO:1 or SEQ ID NO:3 or portions thereof.

As indicated, the present invention provides isolated nucleic acid molecules, including DNA and RNA molecules that encode the DCAL-1 polypeptides disclosed herein. The nucleic acid molecules of the invention may be obtained by amplification from a nucleic acid library, such as a cDNA library, or a genomic library using standard cloning techniques such as those described by Maniatis, et al. (*Molecular Cloning: A Laboratory Manual*, Second Edition, Cold Spring Harbor, N.Y., 1989; which is incorporated herein by reference). Methods for preparing DNA and RNA are well known in the art. In general, RNA is isolated from a tissue or cell that produces large amounts of DCAL-1 RNA. Suitable tissues include lymphoid tissues such as lymph node, spleen and tonsils, as shown in TABLE 1 and further described in Example 2. Total RNA can be prepared using guanidine HCL extraction followed by isolation by centrifugation in a CsCl gradient (Chirgwin, et al., *Biochemistry* 18:52-94, 1979). Poly(A)+ RNA can be prepared from total RNA using the method of Aviv and Leder (*PNAS* 69:1408-1412, 1972). Complementary DNA (cDNA) is prepared from poly(A)+ RNA using known methods. In the alternative, genomic DNA can be isolated. Polynucleotides encoding DCAL-1 are then identified and isolated, for example, using hybridization or PCR.

The isolated nucleic acids of the present invention can also be made using synthetic techniques. Exemplary methods include the phosphotriester method of Narang, et al., *Meth. Enzymol.* 68:90-99 (1979), and the phosphodiester method of Brown, et al., *Meth. Enzymol.* 68:109-151 (1979), e.g., using an automated DNA synthesizer.

The present invention further provides recombinant expression vectors comprising nucleic acid molecules of the present invention. A nucleic acid sequence coding for the desired polypeptide of the present invention, such as, for example, SEQ ID NO:1, can be used to construct a recombinant expression vector which can be introduced into a desired host cell, such as, for example, a bacterial cell, yeast cell or mammalian cell. A recombinant expression vector will typically comprise a polynucleotide of the invention operably linked to transcription initiation regulatory sequences which direct the transcription of the polynucleotide in the intended host cell. Host cells may be genetically engineered (transduced or transformed or transfected) with the expression vectors of this invention. The vector may be, for example, in the form of a plasmid, a viral particle, or a phage. The engineered host cells can be cultured in conventional nutritional media modified as appropriate for activating promoters, selecting transformants that contain the DCAL-1 genes.

In one aspect, the invention provides methods of making a polypeptide comprising SEQ ID NO:2 or SEQ ID NO:4 comprising the steps of culturing a cell into which has been introduced an expression vector of the invention under conditions whereby the DNA segment is expressed and the polypeptide is produced; and recovering the polypeptide. The methods of this aspect of the invention can be practiced using a variety of host cells, including yeast cells, mammalian cells, plant cells and bacterial cells.

Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). The DCAL-1 polypeptides of the present invention can also be expressed in filamentous fungi, for example, strains of the fungi Aspergillus (McKnight, et al., U.S. Pat. No. 4,935, 349, which is incorporated herein by reference). Expression of cloned genes in cultured mammalian cells and in *E. coli*, for example, is discussed in detail in Sambrook, et al. (*Molecular Cloning: A Laboratory Manual*, Second Edition, Cold Spring Harbor, N.Y., 1989; which is incorporated herein by reference). As would be evident to one skilled in the art, one could express the polypeptides of the instant invention in other host cells such as avian, insect and plant cells using regulatory sequences, vectors and methods well established in the literature.

Within one embodiment of this aspect of the invention, the DCAL-1 polypeptides are expressed in mammalian cells. Mammalian expression vectors typically comprise an origin of replication, a suitable promoter and enhancer and also any necessary ribosome binding sites, polyadenylation site, splice donor and acceptor sites, transcriptional termination sequences and 5' flanking nontranscribed sequences. In general, strong transcription promoters will be used, such as promoters from SV40 or cytomegalovirus. Other suitable promoters include those from metallothionien genes and the adenovirus late promoter. Methods for introducing exogenous DNA into mammalian host cells include calcium phosphate-mediated transfection (Wigler, et al., *Cell* 14:725, 1978; Corsaro and Pearson, *Somatic Cell Genetics* 7:603, 1981: Graham and Vander, *Virology* 52:456, 1973), electroporation (Neumann, et al., *EMBO J.* 1:841-845, 1982) and DEAE-dextran mediated transfection (Ausubel, et al., eds., *Current Protocols in Molecular Biology*, John Wiley and Sons, Inc., NY, 1987), which are incorporated herein by reference. Cationic lipid transfection using commercially available reagents including the Boehringer Mannheim Transfection-Reagent (N-[1-(2,3-Dioleoyloxy)propyl]-N—,N,N-trimethyl ammoniummethylsulfate; Boehringer Mannheim, Indianapolis, Ind.) or LIPOFECTIN reagent (N-[1-(2,3-dioleyloxy)propyl]-N,N,N-trimethyl-ammonium chloride and dioeleoyl phosphatidylethanolamine; GIBCO-BRL, Gaithersburg, Md.) using the manufacturer-supplied directions, may also be used. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham, et al., *J. Gen. Virol.* 36:59-72, 1977) cell lines. In one embodiment, the preferred cell line is Chinese hamster ovary (e.g., CHO-K1, ATCC No. CCL 61; or CHO DG44, Chasin, et al., *Som. Cell Molec. Genet.* 12:555, 1986) cell lines. Additional suitable cell lines are known in the art and available from public depositories such as the American Type Culture Collection, Rockville, Md.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a DCAL-1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

The DCAL-1 polypeptides of the present invention expressed using the methods described herein may be isolated and purified by conventional procedures, including separating the cells from the medium by centrifugation or filtration, precipitating the proteinaceous components of the supernatant or filtrate by means of a salt, for example, ammonium sulfate, or ethanol precipitation, acid extraction, purification by a variety of chromatographic procedures, such as, for example, ion exchange chromatography or affinity chromatography, phosphocellulose chromatography, hydrophobic interaction chromatography, hydroxylapatite chromatography and lectin chromatography. Protein refolding steps can be used, as necessary, in completing configuration of the mature protein. Finally, high performance liquid chromatography can be employed for final purification steps.

In another aspect, the present invention provides isolated polypeptides comprising the DCAL-1 amino acid sequence of SEQ ID NO:2 or SEQ ID NO:4 or portions or minor variations thereof that retain at least some of the identifying biological characteristics of DCAL-1. DCAL-1 polypeptides are characterized in that they contain features typical of a type II transmembrane protein with a single extracellular CRD-like domain comprising, or substantially similar to the amino acid sequence CPAKDWKVHKGKCYWIAETKKSWNKSQNDCAINNSYLMVIQD (SEQ ID NO:13), corresponding to amino acid residue 173 to 214 of SEQ ID NO:2 and amino acid residue 117 to 158 of SEQ ID NO:4. The alignment of SEQ ID NO:4 with related C-type lectins, accomplished using CLUSTAL W suggests that the CRD of DCAL-1 (SEQ ID NO:13) is not a standard CRD, but, rather, a truncated form of CRD. For a complete CRD, six conserved cysteine residues, which generate three intrachain disulfide bonds, are required, whereas DCAL-1 only possesses three cysteines (see Kogelberg et al., *Curr. Opin. Struct. Biol.* 11:635, 2001). It is likely therefore, that DCAL-1 generates one intrachain disulfide bond and possibly an interchain disulfide bond to form a dimer or multimer. Notably, there is no obvious $Ca^{2+}$ binding site present in the full length DCAL-1 polypeptide, suggesting a $Ca^{2+}$ independent function. The long form of DCAL-1, shown as SEQ ID NO:2 encoded by SEQ ID NO:1, contains a stalk region (peptides 106 to 161 of SEQ ID NO:2) separating the CRD from the transmembrane region. This longer stalk region may enhance the molecule's flexibility and allow it to project above other molecules on the cell membrane, therefore binding to its ligand more efficiently. The human b-glucan receptor/dectin-1 also has a similar splicing pattern with two stalk regions of varying length separating the transmembrane region from the CRD (see Willment, et al., *J. Biol. Chem.* 276:43818 (2001).

Most C-type lectins play an important role in the recognition of pathogens and the activation of host defense pathways controlling and coordinating innate and adaptive immune responses. See Figdor, et al., *Nat. Rev. Immuno.* 2:77, 2002. Accordingly, DCAL-1 and inhibitors of DCAL-1 have a variety of therapeutic applications. These therapeutic applications include treatment of diseases which require immune regulation, including autoimmune diseases such as rheumatoid arthritis, multiple sclerosis, myasthenia gravis, systemic lupus erythematosis and diabetes. DCAL-1 is useful in modulating the immune system; DCAL-1 and/or DCAL-1 antagonists may be used for reducing graft rejection and preventing graft-versus host disease. In some embodiments, the DCAL-1 polypeptides of the invention are useful for boosting immunity to infectious diseases, treating cancer, treating immunocompromised patients, and improving vaccines as further described herein. The DCAL-1 polypeptides of the invention can also be used in therapeutic applications such as for modulating immune cell to cell interactions, as a T cell costimulatory molecule to enhance Th2 immunity, and to enhance the stimulatory capacity of monocyte derived DCs in an allogenic mixed lymphocyte reaction (MLR), as further described herein.

DCAL-1 polypeptides, DCAL-1 agonists (agents that increase the expression and/or activity of DCAL-1) and DCAL-1 antagonists (agents that decrease the expression and/or activity of DCAL-1) are useful for modulating the expansion, proliferation, activation and stimulation of responsive cell types in vitro, which include both primary cells and cultured cell lines. Of particular interest in this regard are dendritic cells, B cells and T cells. Those skilled in the art will recognize that the DCAL-1 polypeptides of the invention can be advantageously combined with other growth factors in culture media.

In one embodiment, this aspect of the present invention provides isolated polypeptides comprising SEQ ID NO:14 (amino acid residues 85 to 223 of SEQ ID NO:2) or SEQ ID NO:15 (amino acid residues 85 to 167 of SEQ ID NO:4) which correspond to the extracellular domain of the DCAL-1 receptor and therefore comprise DCAL-1 soluble receptors. The DCAL-1 soluble receptors of the invention can comprise additional amino acid residues, such as affinity tags that provide for purification of the polypeptide or provide sites for attachment of the polypeptide to a substrate, or immunoglobulin constant region sequences.

In principle, any peptide or protein for which an antibody or other specific binding agent is available can be used as an affinity tag with the polypeptides of the invention. Non-limiting examples of affinity tags include a poly-histidine tract, protein A (Nilsson, et al., *EMBO J.* 4:1075, 1985), Glu-Glu affinity tag (Grussenmeyer, et al., *Proc. Natl. Acad. Sci. USA* 82:7952-4, 1985), streptavidin binding peptide, and maltose binding protein (Guan, et al., *Gene* 67:21-30, 1987). DNA encoding affinity tags and other reagent are available from commercial suppliers (e.g., Pharmacia Biotech, Piscataway, N.J.).

In one illustrative embodiment, the invention provides polypeptides comprising SEQ ID NO:15 (amino acid residues 85 to 167 of SEQ ID NO:4) operably linked to a histidine tag as described in Example 3.

DCAL-1 soluble receptors of the invention can be used as DCAL-1 antagonists which bind DCAL-1 ligand in vivo or in vitro in therapeutic or other applications where the presence of the DCAL-1 ligand is not desired, as further described herein. DCAL-1 soluble receptors are also useful as a tool to detect cells that express the DCAL-1 ligand as described in Example 6.

The DCAL-1 soluble receptors of the present invention can also be used as a tool to clone the DCAL-1 ligand(s). See, for example, Aldrich, et al., *Cell* 87: 1161-1169, 1996. By way of example, a cDNA expression library prepared from a known or suspected ligand source is transfected into COS-7 cells. The cDNA library vector generally has an SV40 origin for amplification in COS-7 cells, and a CMV promoter for high expression. The transfected COS-7 cells are grown in a monolayer and then fixed and permeabilized. Tagged or biotin-labeled DCAL-1 soluble receptor, described herein, is then placed in contact with the cell layer and allowed to bind cells in the monolayer that express an anti-complementary molecule, i.e., a DCAL-1 ligand. A cell expressing a ligand will thus be bound with receptor molecules. An anti-tag antibody (anti-Ig for Ig fusions, M2 or anti-FLAG for FLAG-tagged fusions, streptavidin, anti-Glu-Glu tag, and the like) which is conjugated with horseradish peroxidase (HRP) is used to visualize these cells to which the tagged or biotin-labeled DCAL-1 soluble receptor has bound. The HRP catalyzes deposition of a tyramide reagent, for example, tyramide-FITC. A commercially-available kit can be used for this detection (for example, Renaissance TSA-Direct.™ Kit; NEN Life Science Products, Boston, Mass.). Cells which express DCAL-1 receptor ligand will be identified under fluorescence microscopy as green cells and picked for subsequent cloning of the ligand using procedures for plasmid rescue as outlined in Aldrich, et al., supra., followed by subsequent rounds of secretion trap assay, or conventional screening of cDNA library pools, until single clones are identified. See also Linsley, et al., *PNAS* 87:5031 (1990).

In some embodiments, the invention provides pharmaceutical compositions comprising DCAL-1 polypeptides, such as full length DCAL-1 polypeptides (SEQ ID NO:2 or SEQ ID NO:4), portions thereof (such as SEQ ID NO:13) or DCAL-1 soluble receptor polypeptides (such as polypeptides comprising SEQ ID NO:14 or SEQ ID NO:15) of the invention, in combination with a pharmaceutically acceptable vehicle. A composition is said to be a pharmaceutically acceptable carrier if its administration can be tolerated by a recipient animal such as, for example, sterile phosphate-buffered saline, buffered saline, or 5% dextrose in water. Other suitable carriers are well-known to those in the art. See, for example, Gennaro, *Reminton's Pharmaceutical Sciences*, 19th Edition (Mack Publishing Company, 1995). Such formulations are useful for topical or parenteral (intravenous or subcutaneous) delivery according to conventional methods. Formulations may further include one or more excipients, preservatives, solubilizers, buffering agents, and albumin to prevent protein loss of vial surfaces. Pharmaceutical compositions comprising DCAL-1 polypeptides can be used in an animal in dosages in the range of about 0.05 to about 500 mg/day, more preferably about 0.1 to about 250 mg/day and most preferably about 0.2 to about 100 mg/day. Determination of dosage is within the level of ordinary skill in the art. Dosing can be daily or intermittently over the period of treatment. Intravenous administration will be by bolus injection or infusion over a typical period of one to several hours. Sustained release formulations can also be employed. In general, a therapeutically effective amount of DCAL-1 is an amount sufficient to produce a clinically significant change in the treated condition, such as a clinically significant change in immune function.

Gene therapy provides an alternative therapeutic approach for delivery of DCAL-1 polypeptides. In one embodiment, a nucleic acid molecule of the invention, such as SEQ ID NO:1 or SEQ ID NO:3 or portions thereof, is introduced into a mammal in a viral vector. Such vectors include an attenuated or defective DNA virus, such as, for example, herpes simplex virus (HSV), papillomavirus, Epstein Barr virus (EBV), adenovirus, adeno-associated virus (AAV), and the like. The vector may then be introduced into a human or animal subject in need of such treatment. Alternatively, a vector encoding DCAL-1 polypeptides can be introduced by lipofection using liposomes. Synthetic cationic lipids can be used to prepare liposomes for in vivo transfection of a gene encoding a marker (see Felgner, et al., *Proc. Natl. Acad. Sci. USA* 84:7413-7, 1987).

In another aspect, the present invention provides antibodies or fragments derived from antibodies that specifically bind to DCAL-1 polypeptides or portions thereof. DCAL-1 polypeptides, including derivatives thereof, as well as portions or fragments of these polypeptides, are utilized as immunogens to prepare the antibodies of the invention. The DCAL-1 polypeptide immunogen may be a full-length polypeptide, such as, for example, SEQ ID NO:2 or SEQ ID NO:4, or may be a portion thereof, such as a portion comprising the CDR region (SEQ ID NO:13), or a portion comprising the extracellular domain (SEQ ID NO: 14 or SEQ ID NO: 15). Immunogenic peptides may be as small as 5 residues. Polypeptides useful for immunization also include fusion polypeptides, such as fusions of amino acid residues comprising SEQ ID NO:14 (comprising amino acids residues 85 to 223 of SEQ ID NO:2) or amino acid residues comprising SEQ ID NO:15 (comprising amino acid residues 85 to 167 of SEQ ID NO:4) with an immunoglobin polypeptide, a histidine tag, or a maltose binding protein.

Antibodies are defined to be specifically binding if they bind to a DCAL-1 polypeptide or a portion thereof with an affinity at least 10-fold greater than the binding affinity to control (non-DCAL-1) polypeptide. It is preferred that the antibodies exhibit a binding affinity $K_a$ of $10^6$ $M^{-1}$ or greater, preferably $10^7$ $M^{-1}$ or greater, more preferably $10^8 M^{-1}$ or greater, and most preferably $10^9 M^{-1}$ or greater. The affinity of a monoclonal antibody can be readily determined by one of ordinary skill in the art (see, for example, Scatchard, *Ann. NY Acad. Sci.* 51:660-672, 1949).

Methods for preparing polyclonal and monoclonal antibodies have been well described in the literature, (for example, see Sambrook, et al., Hurrell, J. G. R., Ed., *Monoclonal Hybridoma Antibodies: Techniques and Applications*, CRE Press, Inc., Boca Raton, Fla., 1982). Such antibodies can be of any immunoglobulin class including IgG, IgM, IgE, IgA, IgD and any subclass thereof. As would be evident to one of ordinary skill in the art, polyclonal antibodies can be generated from a variety of warm-blooded animals such as horses, cows, sheep, dogs, chickens, rabbits, mice and rats. The immunogenicity of a DCAL-1 polypeptide may be increased through the use of an adjuvant such as aluminum hydroxide or Freund's complete or incomplete adjuvant.

In one embodiment of this aspect of the invention, monoclonal antibodies are provided that specifically bind to DCAL-1 polypeptides. Any technique which provides antibodies produced by continuous cell line cultures can be used to prepare the monoclonal antibodies of the invention. Non-limiting examples include the hybridoma technique (Kohler and Milsten, *Nature* 256:495-497, 1975, the trioma technique, the human B-cell hybridoma technique (Kozbor, et al., *Immunology Today* 4:72, 1983) and the EBV-hybridoma technique to produce human monoclonal antibodies (Cole, et al., in *Monoclonal Antibodies and Cancer Therapy*, Alan R. Liss, Inc., pp. 77-96, 1985). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991.

In one embodiment, the invention provides the anti-DCAL-1 monoclonal antibody designated UW50 and the hybridoma cell line producing the UW50 antibody referred to as cell line 2G4.2C1.B5 (ATCC Deposit No. PTA-9866, deposited on Mar. 3, 2009, with the American Type Culture Collection, 12301 Parklawn Drive, Rockville, Md. 20852) as further described in Example 4.

Chimeric antibodies and humanized antibodies for use in the present invention may be generated. A chimeric antibody has at least one constant region domain derived from a first mammalian species and at least one variable region domain derived from a second distinct mammalian species (see, e.g., Morrison, et al., *Proc. Natl. Acad. Sci. USA* 81:6851-55, 1984). Most commonly, a chimeric antibody may be constructed by cloning the polynucleotide sequences that encode at least one variable region domain derived from a non-human monoclonal antibody, such as the variable region derived from a murine, rat, or hamster monoclonal antibody, into a vector containing sequences that encode at least one human constant region. (See, e.g., Shin, et al., *Methods Enzymol.* 178:459-76, 1989; Walls, et al., *Nucleic Acids Res.* 21:2921-29, 1993). The human constant region chosen may depend upon the effector functions desired for the particular antibody. Another method known in the art for generating chimeric antibodies is homologous recombination (U.S. Pat. No. 5,482,856). Preferably, the vectors will be transfected into eukaryotic cells for stable expression of the chimeric antibody.

Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second distinct mammalian species. Most commonly, a chimeric antibody has murine variable region sequences and human constant region sequences. Such a murine/human chimeric immunoglobulin may be "humanized" by grafting the complementarity determining regions, which confer binding specificity for an antigen, derived from a murine antibody into human-derived V region framework regions and human-derived constant regions. Fragments of these molecules may be generated by proteolytic digestion, or optionally, by proteolytic digestion followed by mild reduction of disulfide bonds and alkylation, or by recombinant genetic engineering techniques.

This aspect of the invention also provides molecules derived from antibodies that specifically bind the DCAL-1 polypeptide. Such molecules include, for example, non-human, human, or humanized heavy chain and light chain variable regions of any of the above described Ig molecules which may be constructed as single chain Fv (sFv) fragments (single chain antibodies). See, e.g., Bird, et al., *Science* 242:423-426, 1988; Huston, et al., *Proc. Natl. Acad. Sci. USA* 85:5879-5883, 1988. Multi-functional fusion proteins may be generated by linking polynucleotide sequences encoding an sFv in-frame with polynucleotide sequences encoding various effector proteins. These methods are known in the art, and are disclosed, for example, in EP-B1-0318554, U.S. Pat. No. 5,132,405, U.S. Pat. No. 5,091,513, and U.S. Pat. No. 5,476,786.

A variety of assays known to those skilled in the art may be utilized to detect antibodies which specifically bind to DCAL-1. Exemplary assays include concurrent immunoelectrophoresis, radio-immunoassays, radio-immunoprecipitation, enzyme-linked immuno-sorbent assays, dot blots, inhibition or competition assays and sandwich assays (see *Antibodies: A Laboratory Manual, Harlow and Land*, Cold Spring Harbor Laboratory Press, 1988). An additional method for selecting antibodies that specifically bind to a ligand polypeptide or variant or fragment thereof is by phage display (see, e.g., Winter, et al., *Annul. Rev. Immunol.* 12:433-55, 1994; Burton, et al., *Adv. Immunol.* 57:191-280, 1994). Human or murine immunoglobulin variable region gene combinatorial libraries may be created in phage vectors that can be screened to select Ig fragments (Fab, Fv, sFv, or multimers thereof) that bind specifically to a ligand polypeptide or variant or fragment thereof (see, e.g., U.S. Pat. No. 5,223,409; Huse, et al., *Science* 246:1275-81, 1989; Kang, et al., *Proc. Natl. Acad. Sci. USA* 88:4363-66, 1991; Hoogenboom, et al., *J. Molec. Biol.* 227:381-388, 1992; Schlebusch, et al., *Hybridoma* 16:47-52, 1997 and references cited therein).

Antibodies to DCAL-1 may be used for affinity purification of DCAL-1; within diagnostic assays for determining cells expressing DCAL-1; for detecting DCAL-1 protein as a marker of underlying pathology or disease; for immunolocalization within whole animals or tissue sections, including immunodiagnostic applications, for immunohistochemistry; and for screening expression libraries. Antibodies to DCAL-1 are also useful for practicing the methods of the invention disclosed herein.

In one embodiment of this aspect of the invention, the invention provides anti-DCAL-1 antibodies or fragments derived from antibodies, conjugated to a moiety such as, for example, an imaging moiety, a cytotoxic moiety or an antigenic peptide. These conjugated antibodies are useful for diagnosing and treating animals with a disease associated with immune dysfunction. For diagnostic purposes, including in vitro and in vivo diagnostic applications, it is advantageous to employ antibodies conjugated to an imaging moiety, such as for example, direct tags or labels including radionuclides, enzymes, substrates, cofactors, inhibitors, fluorescent markers, chemiluminescent markers, magnetic particles and the like. For therapeutic applications, cytotoxic moieties and antigenic peptides are useful. Illustrative examples of useful cytotoxic moieties that can be conjugated to an anti-DCAL-1 antibody include radioisotopes and polypeptide cytotoxins, such as type I ribosome-inactivating proteins (e.g., saporin, and momordin), type II ribosome-inactivating proteins (e.g., ricin, abrin, and modeccin), tyrosine kinase inhibitors, and immunomodulators (e.g., cytokines, hematopoietic factors and growth factors).

In some embodiments of this aspect of the invention, an anti-DCAL-1 antibody is conjugated to an antigenic peptide derived from a tumor associated antigen or from a pathogen. Some non-limiting examples of such antigens associated with a disease include the prostate specific antigen (associated with prostate cancer), BRCA-1 and BRCA-2 antigens (associated with many adenocarcinomas, including breast cancer, lung cancer, and pancreatic cancer), CA125 (associated with ovarian cancer), MUC-1 (associated with breast cancer), CA19.9 (associated with colorectal, stomach and pancreatic cancers), and TAG-72 (associated with ovarian, stromal and pancreatic cancers) and p53 (associated with various cancers).

In some embodiments, the antigen is from a pathogen. As used herein, a pathogen is an etiolytic agent capable of causing disease. Some non-limiting examples of pathogens include viruses (e.g. hepatitis B, hepatitis C, herpes and HIV-1), viroids, bacteria, fungi, prion and parasites. Examples of antigens derived from pathogens include, for example, gp120 (associated with HIV infection and AIDS), and EBNA-1 (associated with Epstein Barr Virus infection).

The antibody conjugates of the invention may be constructed using a variety of techniques that are known by one of skill in the art. See *Current Protocols in Immunology*, Wiley and Sons, 1999. For example, immunoconjugates can be produced by indirectly conjugating a therapeutic agent to an antibody component (see, for example, Shih, et al., *Int. J. Cancer* 41:832-839 (1988)). Briefly, one standard approach involves reacting an antibody component having an oxidized carbohydrate portion with a carrier polymer that has at least one free amine function and that is loaded with a plurality of drug, toxin, or other therapeutic agent. This reaction results in an initial Schiff base linkage, which can be stabilized by reduction to a secondary amine to form the final conjugate. By way of another example, antigenic peptides can be conjugated by producing fusion proteins comprising an antigenic peptide to the COOH terminus of the heavy chain of an antibody specific for DCAL-1. See Hawiger, et al., *J. Exp. Med.* 194:769-779 (2001).

In another aspect, the present invention provides methods of stimulating an immune response in an animal comprising the step of introducing into the animal an amount of an anti-DCAL-1 antibody sufficient to stimulate an immune response in said animal. The methods of this aspect of the invention are applicable to any animal, including mammals, such as human beings. The methods of this aspect of the invention can be used to stimulate an immune response in any situation where stimulation of an immune response is desired, including immunotherapy in an animal suffering from a disease associated with an antigen, and prophylactically, when it is desired to immunize an animal against an antigen. The anti-DCAL-1 antibody can be introduced alone, in combination with an antigen, or conjugated to an antigenic peptide.

Stimulation of an immune response in an animal is characterized by at least one of the following changes in a component of the immune system that occurs as a result of introduction of the anti-DCAL antibody in accordance with the methods of the invention: an increase in maturation of DCs or other DCAL-1 expressing antigen presenting cells (measured, for example, by an increase of CD80 and MHC II expression as compared to control animals); an increased ability of isolated DCs from the treated animal to induce T cell proliferative responses in comparison to control animals; the increased ability of the antibody-treated animal to mount a T cell proliferative response against a subsequent challenge of antigen as compared to control animal (see Banchereau, J., et al., *Annu. Rev. Immunol.* 18:767-811 (2000)); an improved immune response with respect to either Th2 or Th1 immunity to pathogens (see Pulendran, B., et al., *Science* 293:253-256 (2001)); a change in the isotype or isotype subclass profile produced in response to antigenic challenge due to alteration in the cytokine profile made by DCs, induced by DCs, or other DCAL-1+ antigen presenting cells (see Pulendran, B., et al., *Trends Immunol.* 22(1):41-47 (2001)); a change in the homing pattern of DCs due to changes in the expression of chemokine receptors or chemokines which leads to enhanced responses to pathogens and mitigates inflammatory and autoimmune processes (see Sallusto, et al., *Annu. Rev. Immunol.* 18:593-620 (2000), Cravens, et al., *Immunol. Cell Biol.* 80(5):497-505 (2002), and Luster, *Curr. Opin. Immunol.* 14(1):129-135 (2002)); or a change in expression and response of DCs to defensins (see Yang, et al., *Trends Immunol.* 23(6):291-296 (2002)).

The anti-DCAL antibodies and antibody-antigenic peptide conjugates described herein are useful in the practice of the method of this aspect of the invention. The anti-DCAL-1 antibodies and conjugates can be introduced into an animal in a variety of ways including for example, intravenous, intra-arterial, intraperitoneal, intramuscular, subcutaneous, intrapleural, by perfusion through a regional catheter, or by direct intralesional injection. When introducing therapeutic proteins by injection, the administration may be by continuous infusion or by single or multiple boluses. Additional routes of administration include oral, mucosal-membrane, pulmonary and transcutaneous.

A pharmaceutical composition comprising an anti-DCAL-1 antibody or conjugates can be formulated according to the methods described herein for DCAL-1 polypeptides. Generally, the dosage of administered anti-DCAL-1 antibodies and conjugates will vary depending upon such factors as the subject's age, weight, height, sex, general medical condition and previous medical history. Determination of dosage is within the level of ordinary skill in the art. As an illustration, anti-DCAL-1 antibodies and conjugates can be administered in dosages in the range of about 0.05 to about 500 mg/day, more preferably about 0.1 to about 250 mg/day and most preferably about 0.2 to about 100 mg/day at low protein doses, such as 20 to 100 milligrams protein per dose, given once, or repeatedly although a lower or higher dosage also may be administered as circumstances dictate.

In another aspect, the invention provides methods for targeting a therapeutic agent to a dendritic cell in an animal, comprising the step of introducing an anti-DCAL-1 antibody or fragment thereof conjugated to said therapeutic agent into the animal. The anti-DCAL antibodies and conjugates described herein as well as methods of polypeptide delivery described herein are useful for practicing the method of this aspect of the invention.

In another aspect, the invention provides methods for promoting maturation of cultured immature dendritic cells in vitro, comprising contacting said immature dendritic cells with an amount of an anti-DCAL-1 antibody sufficient to promote dendritic cell maturation in a portion of said cultured cells.

Immature dendritic cells can be obtained, for example, by culturing CD14+ peripheral blood monocytes with GM-CSF and IL-4 as described in Example 9. See also Romani, et al., *J. Immunol. Methods* 196:137, 1996; and Bender, et al., *J. Immunol. Methods* 196:121 (1996). The DCs thus obtained will be in an immature state, generally possessing a high capability for antigen capture and processing, but relatively low T cell stimulatory capacity.

The method of this aspect of the invention comprises the maturation of immature DCs by contacting the immature DCs with an anti-DCAL-1 antibody in an amount and for a time sufficient to promote DC maturation. The anti-DCAL-1 antibodies described herein are useful for the method of this aspect of the invention. It will be understood by one skilled in the art that the DCs are incubated in a tissue culture medium under conditions readily determinable to those of skill in the art. The specific amount of anti-DCAL-1 antibody used and the time of exposure will vary according to a number of factors that will be appreciated by those of skill in the art, including, for example, the origin of the DCs to be matured, the potency and other characteristics of the anti-DCAL-1 antibody used. In some embodiments, it is currently preferred that the anti-DCAL-1 antibody be used at a concentration of about 1 µg/ml to about 100 µg/ml, preferably about 10 µg/ml to about 100 µg/ml.

Maturation of immature dendritic cells is characterized by at least one of the following changes that occurs in cultured immature DCs as a result of exposure to an anti-DCAL-1 antibody in accordance with the methods of this aspect of the invention: increased expression, as compared to an untreated control culture, of MHC class II, or CD40, or CD80, or CD83 or CD86 or HLA-DR; an increase in the release of proinflammatory cytokines; an increased ability to cause proliferation of naive allogenic T cells in a mixed lymphocyte culture; increased expression of CCR7; and a decrease in the level of CCR1 or CCR5 or CD1a.

The cultured immature DCs are contacted with an anti-DCAL antibody for a sufficient amount of time to promote DC maturation. This can be determined by periodically withdrawing samples of the DC containing medium and assaying for one of the above described properties, such as, for example, expression of CD83. Although the time of exposure will vary according to factors understood by those of skill in the art, in general approximately 24 to 48 hours of exposure to an anti-DCAL-1 antibody is typically required to promote DC maturation.

The method of this aspect of the invention is useful for ex vivo cell transplantation immunotherapies. Examples of such therapies include ex vivo cell transplantation therapies for treating disorders of the immune system, such as AIDS; and the ex vivo expansion of T cells, particularly antigen specific T cells which can then be used to treat disorders characterized by deterioration of the immune system; the preparation of antigen activated DC according to methods known in the art; and development of vaccines and vaccine adjuvants.

In another aspect, the invention provides methods for stimulating CD4+ T cells in vitro comprising the steps of contacting said CD4+ T cells with CD3+ and contacting said CD3+ stimulated T cells with a polypeptide comprising SEQ ID NO: 14 (amino acid residues 85 to 223 of SEQ ID NO:2) with a polypeptide comprising SEQ ID NO: 15 (amino acid residues 85 to 167 of SEQ ID NO:4).

The method of this aspect of the invention can be used to expand selected T cell populations for use in treating an infectious disease or cancer. The resulting T cell population can be genetically transduced and used for immunotherapy or can be used for in vitro analysis of infectious agents such as HIV.

Methods for isolating CD4+ T cells are well known to those of skill in the art (see, *Current Protocols in Immunology*, Wiley and Sons, 1999). An anti-CD3 monoclonal antibody, such as OKT3 (obtained from ATCC) can be used to activate a population of T cells via the TCR/CD3 complex. The DCAL-1 soluble receptor polypeptides such as polypeptides comprising SEQ ID NO: 14 or SEQ ID NO: 15 as described herein are useful in the method of this aspect of the invention. T cell proliferation can be measured, for example, by assessing the number of cell divisions using carboxy-fluorescein diacetate succinimidyl ester (CFSE) as further described in Example 7.

In another aspect, the invention provides methods for modulating an immune response in an animal comprising the step of introducing into the animal a soluble DCAL-1 receptor of the invention in an amount sufficient to inhibit an immune response in said animal. The DCAL-1 soluble receptor polypeptides such as polypeptides comprising SEQ ID NO: 14 or SEQ ID NO: 15 as described herein are useful in the method of this aspect of the invention. The methods described herein for in vivo delivery and dosage of polypeptides are also useful in the method of this aspect of the invention.

The methods of this aspect of the invention are useful, for example, to inhibit an immune response in a disease state wherein a large amount of DCAL-1 ligand is expressed. For example, DCAL-1 soluble receptors can be used as a direct antagonist of the ligand in vivo, and aid in reducing progression and symptoms associated with an autoimmune disease such, for example, rheumatoid arthritis, multiple sclerosis, myasthenia gravis, or systemic lupus erythematosis. Moreover, DCAL-1 soluble receptors can be used to inhibit DCAL-1 ligation which is known to lead to activation of dendritic cells as described herein, by binding ligand in vivo that would otherwise bind to DCAL-1.

The following examples merely illustrate the best mode now contemplated for practicing the invention, but should not be construed to limit the invention. All literature citations herein are expressly incorporated by reference.

EXAMPLE 1

This example describes the cloning of DCAL-1 and identification of the DCAL chromosomal location and gene structure.

DCAL-1 Gene Discovery

In order to identify genes expressed in human germinal centers, subtractive hybridization was carried out as follows: enriched follicular dendritic cell (FDC) populations were obtained from human tonsils according to the method of Liu, et al., *J. Exp. Med.* 185:165-170 (1997). Tonsils were cut into small pieces and digested for 12 minutes at 37° C. with an enzyme cocktail in RPMI 1640 medium (GIBCO, BRL Gaithersburg, Md.) containing collagenase IV (1 mg/ml; Sigma Chemical Co., St. Louis, Mo.) and deoxyribonuclease I (50 kU/ml; Sigma Chemical Co.). The cells were collected and a new stock of enzyme solution was added to the remaining tissue fragments for another 12 minutes. After two successive rounds of enzymatic digestions, the cells were collected, pooled and centrifuged through Ficol-Hypaque (Eurobio, Paris, France) for 20 minutes at 400 g to remove dead cells. After two washes, cells were layered on a 1.5% BSA (Pentex® Path-o-cyte 5; Miles Inc., Kankakee, Ill.) gradient and centrifuged at 10 g for 10 minutes at 4° C. The FDC-lymphocyte clusters were recovered from the pellet. This BSA gradient process was repeated two to three times. Cells were pooled and total RNA was isolated.

Double-stranded cDNA was produced using the switching mechanism at RNA termini (SMART) PCR cDNA synthesis method (Clontech). The resulting cDNA was then analyzed by PCR using primers that distinguished FDC and B cell isoforms of CD21 to confirm that both isoforms were present in approximately equal proportions. A double-stranded driver cDNA was produced by the same method using an equal mixture of RNA from the fibroblast cell lines HFF and the epithelial line HeLa. A suppression subtractive hybridization PCR subtraction procedure was carried out according to the manufacturer's protocol (PCR Select; Clontech), using the FDC cDNA as tester and the fibroblast/epithelial cell cDNA as driver. The pool of differentially expressed gene fragments generated was then cloned into the pCRII vector (Invitrogen), and clones were randomly picked and screened for differential expression using tester and driver cDNA probes. Differentially expressed clones were sequenced by dye-terminator sequencing (PE Biosystems).

One of the isolated clones encoded for a novel C-type lectin-like molecule, designated as DCAL-1. A putative translational start site upstream of the transmembrane region was identified in a putative exon in the genomic sequence from human bacterial artificial chromosome (BAC) clone RPC111-75L1, accession no. AC007068, using the GRAIL program (Accelrys, San Diego, Calif.); see also, Xu, et al., *J. Computational Biol.* 4:325 (1997).

Further sequence of the transmembrane and cytoplasmic regions was obtained by 3' and 5' RACE PCR using the SMART RACE cDNA amplification kit (Clontech, Palo Alto, Calif.), and a full-length clone was isolated from cDNA isolated from CD40 ligand (CD40L) stimulated human tonsillar B cells (accession no. AF518873) using the following primers:

5' aaaacgagaacctactgtatgg-3' SEQ ID NO: 5
5'-ctaaatgttaaatctcaccatagca-3' SEQ ID NO:6

The resulting PCR product was cloned into PCR2.1 vector using a TA cloning kit (Invitrogen, San Diego, Calif.). DNA sequencing was completed using the Big Dye cycle sequencing kit and an ABI PRISM 337 DNA sequencer (PE Applied Biosystems, Foster City, Calif.). Five independent clones were obtained which each contained the full-length nucleic acid sequence, shown as SEQ ID NO:1. The nucleic acid sequence of SEQ ID NO:1 encodes the DCAL-1 amino acid sequence shown in SEQ ID NO:2.

Gene Structure and Chromosomal Location

The intron/exon structure of the DCAL-1 gene was deduced by alignment of the sequence and ESTs (GenBank database) with the BAC clone RPC111-75L1, using the program GRAIL. The following ESTs expressed a portion of the DCAL-1 gene: BG213959, AI719511, AW237307, AI879793, BG195772, BG258759, AA746003, BG391322, BG391235, BG391532, XP090246 and AI271437. The comparison between DCAL-1 cDNA sequence and the EST database suggests that there are at least two alternatively spliced forms of DCAL-1. The first splicing site is in the neck region of the lectin, which changes the length of the molecule that extends from the cell surface, but not the intracellular domain or the C-type lectin domain. The long form of the DCAL-1 protein, shown as SEQ ID NO:2 encoded by SEQ ID NO:1, contains a stalk region separating the CRD from the transmembrane region. This longer stalk region may enhance the molecule's flexibility and allow it to project above other molecules on the cell membrane, therefore binding to its ligand more efficiently. The shorter form of the DCAL-1 protein is provided as SEQ ID NO: 4 which is encoded by SEQ ID NO:3. Northern blot analysis (summarized in TABLE 1) confirmed the presence of two different sized DCAL-1 transcripts (7.5 kb and 9.6 kb), indicating that DCAL-1 has two splice variants.

Sequence analysis of the BAC clone RPC111-75L1 indicated that the regions 144735-144928 and 14639-147394 are also possible exons. The EST search revealed that the DCAL-1 locus is within a cluster of C-type lectin loci on human chromosome 12p12-13 just 3' to the CD69 locus as shown in FIG. 1.

EXAMPLE 2

This example provides the results of DCAL-1 mRNA expression analysis by Northern Blot and RT-PCR in a variety of tissue types and cell lines.

Northern Blot Analysis: Analysis of tissue distribution was done by Northern blot using commercially available blots of human RNA (Human Multiple Tissue Northern Blots, Clontech, Palo Alto, Calif.) and to a Northern blot containing 2 μg of total RNA from human tonsils. A probe was obtained by PCR amplification of a 146 bp DNA fragment corresponding to SEQ ID NO:3 spanning base pairs 169 to 315. The PCR product was purified and the DNA was radioactively labeled with $^{32}P$ using a commercially available kit (Amersham Corp., Arlington Heights, Ill.). The probes were hybridized, washed and exposed according to manufacturer's protocol (Clontech). A GP3DH probe was used as a positive control.

Results: As shown below in TABLE 1, DCAL-1 mRNA is highly expressed in lymphoid tissues including spleen, lymph node, and tonsil and at lower levels in peripheral blood, bone marrow, and colon. Two major transcripts of different sizes were observed on the Human Multiple Tissue blots at about (7.5 kb) and (9.5 kb) indicating that DCAL-1 has two splice variants.

TABLE 1

Northern Blot Analysis of DCAL-1 Expression

| Tissue | DCAL-1 Expression (Northern blot) |
| --- | --- |
| Bone Marrow | + |
| Adrenal Gland | − |
| Trachea | − |
| Lymph Node | +++ |
| Spinal Cord | − |
| Thyroid | − |
| Stomach | − |
| Peripheral Blood Leukocyte | + |
| Colon | + |
| Small Intestine | − |
| Ovary | − |
| Testis | − |
| Prostate | − |
| Spleen | +++ |
| Heart | − |
| Brain | − |
| Placenta | − |
| Lung | − |
| Liver | − |
| Skeletal Muscle | − |
| Kidney | − |
| Pancreas | − |
| Tonsil | ++ |

RT-PCR Analysis: Monocytes were isolated from peripheral blood of healthy donors (American Red Cross, Portland, Ore.) using positive selection with anti-CD14-labeled magnetic beads (Miltenyi Biotec, Auburn, Calif.); the purity of the monocytes obtained was routinely at least 95% pure. CD14$^+$ cells were differentiated into CD11a$^+$ immature dendritic cells in the presence of GM-CSF (Immunex, Seattle, Wash.) and IL-4 (Research Diagnostics, Flanders N.J.) for 5-7 days. The cells were matured to CD83$^+$ dendritic cells by incubating them with mAb to CD40 (G28-5) or *Escherichia coli* LPS (Sigma, St. Louis, Mo.) for 24 or 72 hours.

Human tonsillar B cells were prepared as follows: intact tonsils were minced to give a tonsillar cell suspension. Mononuclear cells were isolated by density gradient centrifugation through Ficoll-Hypaque (Pharmacia) and small resting B cells were enriched by sheep red blood cell (SRBC) rosetting and fractionation in discontinuous percoll density gradients (Pharmacia). Cells with a density greater than that of a 55% percoll solution were selected and stimulated with anti-CD40 or LPS for 24 h (see Barrett, et al., *Eur. J. Immunol.* 20:1053-1059, 1990).

Dendritic cells: BDCA-2$^+$ and CD1c$^+$ dendritic cells were isolated from peripheral blood by positive selection with BDCA-2- and CD1c-labeled magnetic beads (Miltenyi Biotec).

The purified primary cells or cells lines were lysed in TRIzol reagent (Life Technologies/Invitrogen, Carlsbad, Calif.) and RNA was isolated as described by the manufacturer. First-strand cDNA was synthesized using random hexamers and avian myeloblastosis virus reverse transcriptase (Promega, Madison, Wi.). DCAL-1 expression was analyzed by RT-PCR of the cDNA in 10-fold dilutions using the following primers:

DCAL-1 primers
5'-gtgcaatggctggagatgtagtctacgc-3' SEQ ID NO:7
5'-tcactgccagtgtgggggatgctgtc-3' SEQ ID NO:8
G3PDH positive control:
5'-accacagtccatgccatcac-3' SEQ ID NO:9
5'-tccaccaccctgttgctgta-3' SEQ ID NO:10

Results:

B cells: RT-PCR analysis of DCAL-1 expression showed that DCAL-1 mRNA is expressed in every B cell line tested including BJAB, Daudi, Ramos, B104, T-51 and CESS as shown below in TABLE 2. These results suggest that DCAL-1 mRNA is expressed in immature, lymphoblastoid and memory B cell stages. DCAL-1 mRNA was also highly expressed by primary tonsillar B cells and is upregulated upon stimulation with anti-CD40 as shown below in TABLE 3.

T cells: DCAL-1 mRNA is not expressed in T cell lines tested (Jurkat and Molt4), nor is it expressed an epithelial line (HeLa) or the myeloid cell line HL60. See TABLE 2.

Dendritic cells: DCAL-1 mRNA is expressed in both DC peripheral blood subpopulations tested: BDCA-2$^+$ CD11c- CD123bright plasmacytoid DCs and CD1c$^+$ CD11cbright CD123dim myeloid DCs (data not shown).

CD14$^+$ monocytes: Resting CD14$^+$ monocytes do not express DCAL-1 mRNA, however, differentiation of monocytes to CD1a$^+$ immature DCs with GM-CSF and IL-4 up-regulated DCAL-1 mRNA. See TABLE 3. Maturation of immature DCs to CD83$^+$ mature DCs by anti-CD40 or LPS stimulation for 24 h maintains, but does not further enhance DCAL mRNA expression (data not shown).

TABLE 2

RT-PCR Analysis of DCAL-1 Expression in lymphoid cell lines

| Cell Line | DCAL-1 Expression (RT-PCR) |
| --- | --- |
| FDC Tester | + |
| Epithelial/fibroblast driver | − |
| Jurkat Cells | − |
| Molt4 | − |
| BJAB | + |
| Daudi | + |
| Ramos | + |
| B104 | + |
| T-51 | + |
| CESS | + |
| HL60 | − |
| HeLa | − |

TABLE 3

RT-PCR Analysis of DCAL-1 expression in Monocytes and Dendritic Cells

| Cell Type | DCAL-1 expression (RT-PCR) |
| --- | --- |
| CD14+ Monocytes | − |
| CD1a+ immature DC (CD14+ monocytes cultured for 7 days with GM-CSF and IL-4) | + |
| Resting B cells | + |
| B cells stimulated with anti-CD40 | ++ |

EXAMPLE 3

This example describes the construction of a plasmid encoding soluble DCAL-1-His receptor conjugated to a polyhistidine tag.

Plasmid Construction An expression plasmid encoding a six-His-tagged extracellular region of DCAL-1 (encoding SEQ ID NO:15) was constructed using the QIA Express kit (Qiagen, Chatsworth, Calif.). To construct the expression vector, the following primers were used to amplify SEQ ID NO:3:

5'-gttgttggatccaatcaaaactgttcggacttccccg-3' (BamH1) SEQ ID NO:11

5'-cgcaagctttgttcattcaactaatatttgtatag-3' (HindIII) SEQ ID NO:12

The PCR product was digested with BamH1+HindIII and cloned into the pQE-31 expression vector (Qiagen). A control plasmid was constructed in parallel containing the extracellular region of DC-SIGN (Curtis, et al., *Proc. Natl. Acad. Sci. USA* 89:8356, 1992). The constructs were transfected into *E. Coli* M15 (pREP4) and the bacteria were grown in Luria-Bertonia broth supplemented with ampicillin (100 µg/ml) and kanamycin (25 µg/ml). Protein expression was induced with 1 mM isopropyl-B-D-galactopyranoside. The proteins were solubilized in urea, purified by chromatography on a nickel-nitrilo-triacetic acid resin column (Qiagen) as directed by the manufacturer. The proteins were then refolded by stepwise dialysis as described in Steinle, et al., *Immunogenetics* 53:279, 2001. Solubilized proteins were incubated with 5 mM reduced glutathione and 0.5 mM oxidized glutathione for 24 hours at 5° C. and successively dialyzed against decreasing concentrations of urea (4 M, 2 M, 1 M, no urea) in 0.1 M Tris pH 8.0, 0.4 M L-arginine, 1 mM EDTA, 0.1 mm phenylmethylsulfonyl fluoride. Refolded proteins were dialyzed against PNEA (50 mm PIPES pH 7.0, 0.15 m NaCl, 1 mM EDTA, 0.02% $NaN_3$). Protein preparations were examined by sodium dodecylsulfate-polyacrylamide gel electrophoresis (SDS-PAGE) and immunoblotting.

EXAMPLE 4

This example describes the production of monoclonal antibodies specific to DCAL-1 polypeptides.

Methods: To make antibodies specific to DCAL-1, the polypeptides DCAL-1-His, and control protein DC-SIGN-His, were made as described in Example 3. BALB/c mice were injected intraperitoneally with each polypeptide formulated with monophosphoryl lipid A, and trehalose dicorynomycolate emulsion (Corixa, Hamilton, Mont.) as adjuvant. Mice were boosted at weeks two and ten. Three days following the final boost, spleens were removed and hybridomas were made by fusion with NS-1 cells. See *Current Protocols in Immunology*, Section 2.5.1-2.5.17, Wiley and Sons, 1999.

An ELISA screen using the DCAL-1 and DC-SIGN proteins was used to determine positive clones. Any sample that was positive for both DCAL-1 and DC-SIGN was eliminated as a false positive. One clone, designated UW50 (IgM) was positive for DCAL and negative for DC-SIGN in the ELISA screen and upon further subcloning, retained these characteristics. The hybridoma cell line referred to as cell line 2G4.2C1.B5 (ATCC Deposit No. PTA-9866) that produces the anti-DCAL-1 monoclonal antibody referred to as UW50 has been deposited in the American Tissue Type Collection, 12301 Parklawn Drive, Rockville, Md. 20852 on Mar. 3, 2009.

EXAMPLE 5

This example describes the analysis of cell surface expression of DCAL-1 using an anti DCAL-1 mAb binding assay on a variety of lymphoid cell lines and primary cells.

Preparation of Cells:

Cell lines tested: BJAB; Jurkat

Primary dense tonsillar B cells:

$CD14^+$ monocytes were isolated by positive selection from peripheral blood.

$CD3^+$ T cells were isolated from peripheral blood of different donors.

$CD1a^+$ immature DC: Monocytes were differentiated to $CD1a^+$ immature DCs with GM-CSF and IL-4.

$BDCA-2^+$ DCs were isolated from peripheral blood.

Binding with anti DCAL-1 mAb: The above primary cells and cell lines were incubated with the DCAL-1 mAb (UW50), produced as described in Example 4, or the isotype control (mouse IgM), followed by rat anti-mouse IgM-FITC (BioSource, Camarillo, Calif.). DCAL-1 protein expression on the cell surface was then determined by flow cytometry on a FACScan analyzer (BD Biosciences, Mountain View, Calif.). Results shown in TABLE 4 are representative of three independent experiments.

Results: TABLE 4 presents the expression profile of DCAL-1 protein on the surface of lymphoid cells as determined by staining with a DCAL-1 mAb (UW50), followed by flow cytometry. As shown below in TABLE 4, B cell line BJAB and primary dense tonsillar B cells expresses high levels of DCAL-1 protein. The level of surface DCAL-1 expression on B cells is not further enhanced following stimulation with recombinant CD40L (1 ug/ml). DCAL-1 expression was not observed in the Jurkat T cell line, nor in peripheral blood $CD3^+$ T cells.

TABLE 4

Summary of DCAL-1 Protein Expression

| Cell line | DCAL-1 protein expression (as measured by percent of cells binding to UW50mAb) |
|---|---|
| BJAB | 95% |
| Dense Tonsillar B Cells | 85% |
| Dense Tonsillar B Cells stimulated with CD40L | 86% |
| CD14+ Monocytes | 0% |
| CD1a+ immature DCs | 65.6% |
| CD40L stimulated DCs | 72.2% |
| Jurkat T cells | 0% |
| CD3+ T Cells from PBMCs | 0% |

Figure 2C:
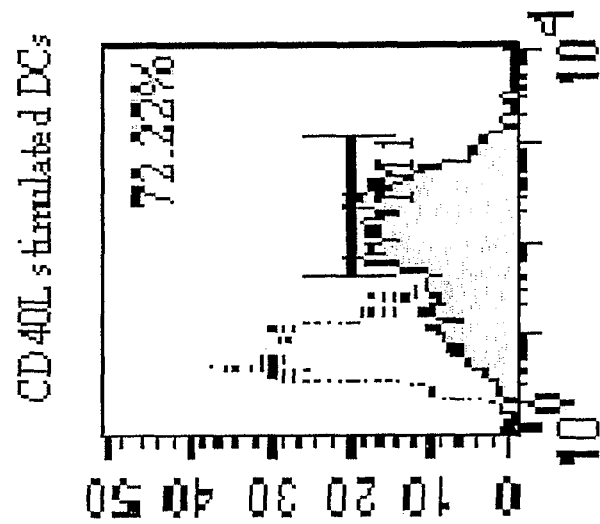
FIG. 2C demonstrates that DCAL-1 expression is maintained after stimulation of DCs with CD40L (1 µg/ml for 24 h), as described in Example 5.
Figure 2B:
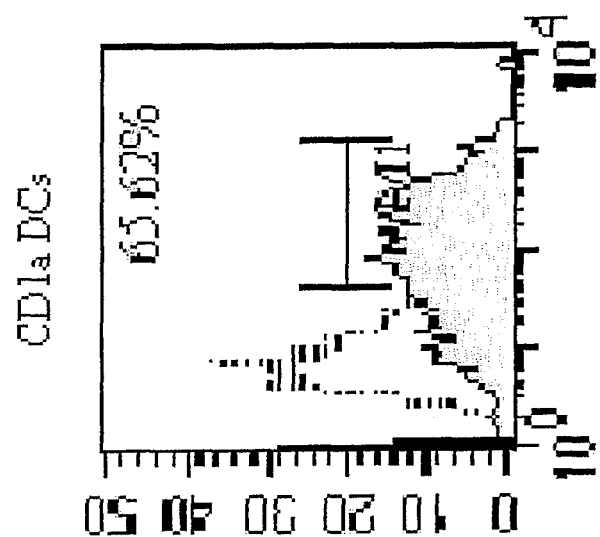
FIG. 2B demonstrates that differentiation of monocytes to CD11a+ immature DCs (with GM-CSF and IL-4) induces the expression of DCAL-1 protein.
Figure 2A:
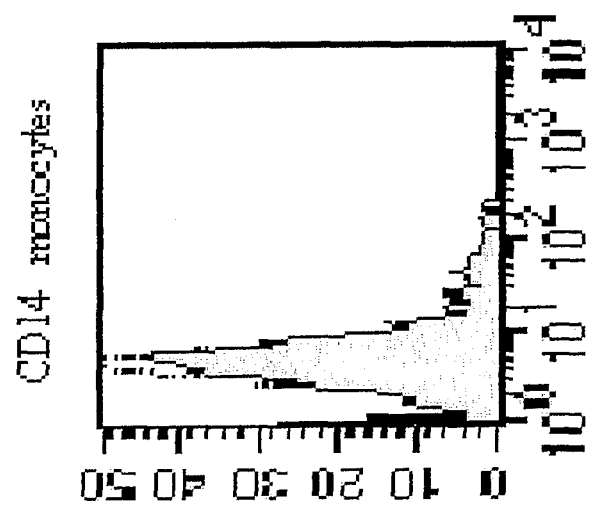
FIG. 2A demonstrates that CD14+ monocytes isolated by positive selection from peripheral blood do not express DCAL-1.

FIG. 2 shows the DCAL-1 protein expression profile before and after the differentiation of monocytes to immature DCs. As shown in FIG. 2A, $CD14^+$ monocytes isolated by positive selection from peripheral blood do not express DCAL-1. However, differentiation of CD14+ monocytes to $CD1a^+$ immature DC's (with GM-CSF and IL-4) induces the expression of DCAL-1 protein as shown in FIG. 2B. DCAL-1 protein expression is maintained after stimulating the cells with CD40L (1 ug/ml for 24 h) as shown in FIG. 2C.

Figure 3B:
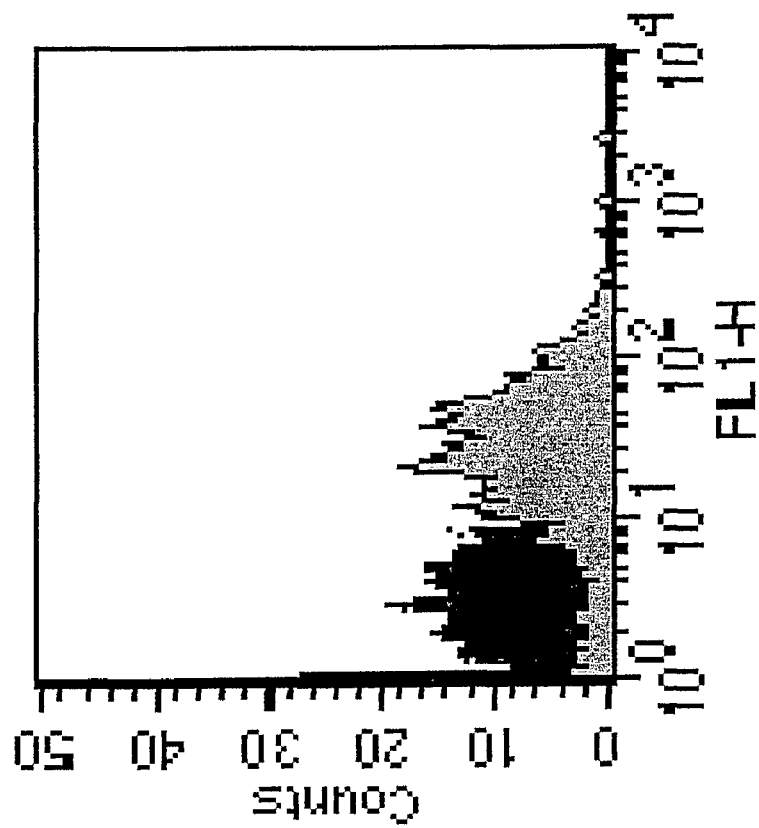
FIG. 3B demonstrates that DCAL-1 is expressed on the surface of CD1c+ DCs as described in Example 5.
Figure 3A:
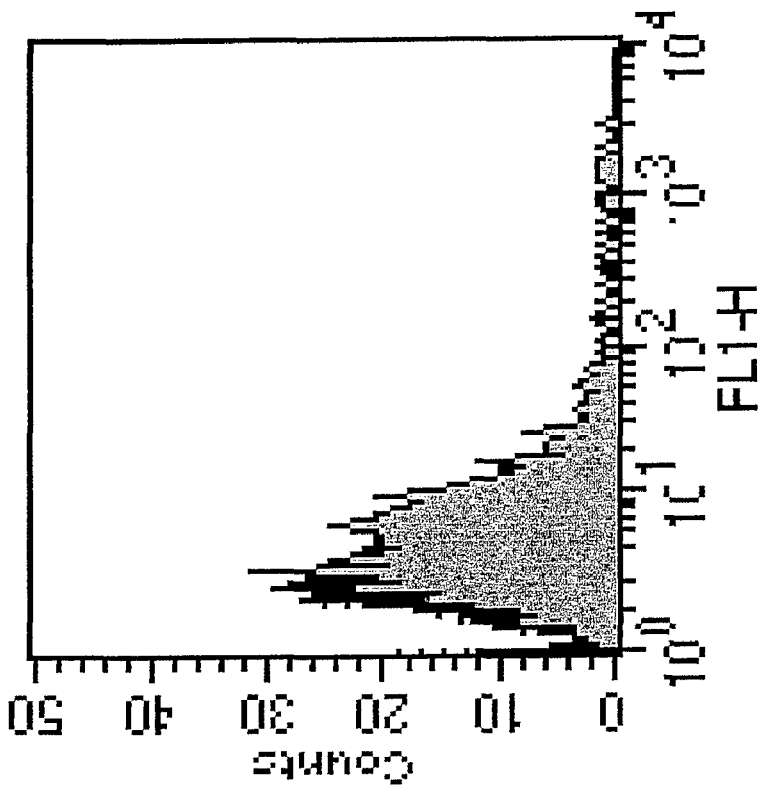
FIG. 3A demonstrates that DCAL-1 is not expressed on the surface of BDCA-2+ DCs isolated from peripheral blood, as described in Example 5.

FIG. 3 shows the expression profile of DCAL-1 protein in various DC subsets. As shown in FIG. 3A, DCAL-1 is not expressed on the surface of BDCA-2+ DCs isolated from peripheral blood. However, as shown in FIG. 3B, DCAL-1 is expressed on the surface of CD1c+DCs.

In summary, the expression pattern of DCAL-1 on DCs differs from the expression profile observed for other recently described DC associated, C-type lectins such as DCIR, which is down-regulated by DC maturation stimuli (such as LPS, TNF-alpha and CD40L) (see e.g. Bates, et al., *J. Immunol.* 163, 1973). Moreover, activation of immature DCs by anti-CD40 or LPS stimulation maintains DCAL-1 protein expression suggesting that DCAL-1 may play a role in either antigen uptake or antigen presentation.

EXAMPLE 6

This example demonstrates that a DCAL-1 ligand is expressed on naïve T cells and B cells in peripheral blood by using the DCAL-1-His soluble receptor to assay binding on peripheral blood mononuclear cells (PBMCs) and dense tonsillar cells.

Methods: PBMC from healthy donors and dense tonsillar B cells were incubated with 10 µg of DCAL-1 soluble receptor (DCAL-1-His) or an unrelated control soluble fusion protein (DC-SIGN-His), made as described in Example 3. Binding was detected by the six-His-specific biotinylated Ab (Berkeley Antibody, Richmond, Calif.) at 10 µg/ml, followed by streptavidin-PerCP (BD PharMingen). In some experiments cells were also stained for different lineage markers with FITC- and PE-conjugated Abs (BD PharMingen); CD14-FITC (MφPG), CD16-FITC (NKP15), CD20-FITC (1F5), CD19-PC5 (J4.119), CD45RA-FITC (L48), CD45RO-PE (UCHL-1), CD4-PE (SK3), CD8-FITC (SK1), and CD3-PE (SK7). His tagged protein binding to the cell subsets was then analyzed by flow cytometry. Results shown in TABLE 5 are representative of six independent experiments with cells isolated from five individual donors and are gated on the lymphocyte population of PBMC.

In a separate experiment, PBMC were incubated with DCAL-1-His followed by anti-His-biotin, streptavidin-PerCP, anti-CD45RA-FITC, and either anti-CD4-PE or anti-CD8-PE.

Results: As shown in TABLE 5, DCAL-1-His binds to a population of CD20+ peripheral blood B cells, but not dense tonsillar B cells. In contrast, the control DC-SIGN-His fusion protein did not bind to CD20+ peripheral blood B cells (data not shown). As shown in TABLE 5, DCAL-1-His binds to a significant population of CD45RA+ T cells, but does not bind to CD45RO+ T cells. The control DC-SIGN binds to a population of CD45RA+ but does not bind to a population of CD45RO+ T cells (data not shown). The majority of cells that bound to DCAL-1-His were CD4+CD45+RA+PBMCs. DCAL-1-His did not bind to CD8+CD45+RA+PBMCs (data not shown).

TABLE 5

Binding of DCAL-1-His Soluble Receptor to naïve T cells and B cells

| Cell Type | Percentage of cells bound to DCAL-1-His |
|---|---|
| CD20+ B Peripheral Blood B Cells | 7.34% |
| Dense Tonsillar B Cells | 0% |
| CD45+RA+ T Cells | 7.8% |
| CD45+RO+ T Cells | 1.3% |

In summary, the results demonstrate that a DCAL-1 ligand is expressed on naïve T cells and B cells in peripheral blood. The binding pattern of DCAL-1-His to B cells and to a subset of T cells suggests that DCAL-1 may function in mediating immune cell to cell interactions.

EXAMPLE 7

This example demonstrates that DCAL-1-His can be used as a T cell costimulatory molecule to enhance anti-CD3 induced proliferation of CD4+ T cells and increase T cell secretion of IL-4.

Preparation of cells: Total CD3+ T cells were isolated from PBMC by sheep red blood cell (SRBC) agglutination (SRBCs from Triple J Farms, Bellingham, Wash.). The CD3+ cells isolated were routinely >97% pure. CD4+ T cells were isolated by panning with CD8 mAb (G10-1) and CD8+ cells were isolated by panning with CD4+ mAm OKT4 for 1 hour at 37° C. CD4+ CD45RA+ T cells were purified by negative selection using anti-CD45RO-labeled microbeads (Miltenyi biotec, Auburn, Calif.). Carboxy-fluorescein diacetate, succinimidyl ester (CFSE) (Molecular Probes, Eugene, Ore.) labeling of CD4+ and CD8+ T cells was performed as described in Matthews, et al., *J. Immunol.* 164:6206 (2000). Total T cells or CD4+ CD45RA+ T cells were coincubated with CD3 mAb (64.1) at 1, 0.3, 0.1, and 0 µg/ml (in solution), with either media alone, or with 0.5, 1, 5, 10 and 25 µg/ml of DCAL-1-His or DC-SIGN-His fusion proteins for 5 days at 37° C. in 5% $CO_2$. All cells were cultured in complete RPMI 1640 with 10% FCS and 50 µm 2-ME. The number of cell divisions was assessed by analyzing CFSE dye extinction with a FACScan. Supernatants were removed and frozen at −20° C. for cytokine analysis.

Cytokine Analysis: IL-4 and IFN-γ secretion were analyzed by capture immunoassay in triplicate using matched pairs of cytokine-specific mAbs as follows: capture anti-IL-4 (8D4-8); detection anti-IL-4 (Mp4-25D2); capture IFN-γ (NIB42), detection IFN-γ (4S.B3) (BD PharMingen). Concentrations of cytokines were extrapolated from a standard curve prepared with recombinant cytokine (BD PharMingen). Detection limits of the assay were 15 pg/ml for IL-4 and 1.25 ng/ml for IFN-γ. Results shown in FIGS. 4A-D are expressed as the mean (±SD) of triplicate cultures of T cells (p<0.0001 vs control by Student's t test). Results are representative of four independent experiments with cells isolated from four different donors.

Cytokine production was also detected by intracellular cytokine staining as described in Pala, et al., *J. Immunol. Methods* 243:107 (2000). Cells were stimulated as described above, but for the last 6 h of culture, PMA (25 ng/ml:Sigma), ionomycin (100 ng/ml: Calbiochem), and Golgi-Stop (as recommended by the manufacturer, BD PharMingen) were added. Cells were then washed, fixed with 4% paraformaldehyde, permeabilized with 0.1% saponin/1% FCS/PBS, and labeled with anti-IL-4-PE (8D4-8,BD PharMinogen) or IgG1-PE isotype control. The cells were analyzed by flow cytometry and results were analyzed using CellQuest software (BD Biosciences).

Results: Results shown in FIG. 4 are representative of three independent experiments with cells isolated from three individual donors. Co-incubation of T cells with the DCAL-1-His protein and anti-CD3 enhanced proliferation, even at very low doses of soluble CD3 mAb (0.1 µg/ml) as shown in FIG. 4 panels A and B. As shown in panel C, DC-SIGN-His was less effective at stimulating T cells. Incubation with DCAL-1-His or DC-SIGN-His alone had no effect of proliferation. Co-incubation with DCAL-1-His increased the percentage of cells proliferating from 35.45% with anti-CD3 alone to 74.65% (FIG. 4B). Co-incubation with DC-SIGN-His protein (control) increased the percentage of proliferating cells from 35.45 to 50.22% (FIG. 4C).

As shown in FIG. 5A, the DCAL-1-His soluble receptor significantly increased the secretion of IL-4 by anti-CD3-stimulated T cells in a dose dependant manner with the optimum dose of DCAL-1-His at 10 µg/ml, whereas the control DC-SIGN-His soluble receptor did not affect the secretion of IL-4 (see FIG. 5B). However, DCAL-1-His costimulation did not cause the T cell response to be completely polarized to Th2, as IFN-γ secretion was not inhibited in the presence of DCAL-1-His (FIG. 5D) or in the negative control DC-SIGN-His (see FIG. 5C).

In addition, in a separate experiment intracellular cytokine staining of IL-4 demonstrated that IL-4 production is increased nearly two-fold (M.F.I. 43.4) after costimulation with the DCAL-1-His soluble receptor and anti-CD-3, as compared to IL-4 production after anti-CD-3 stimulation alone (M.F.I. 26.8).

In summary, the results illustrate that the DCAL-1-His soluble receptor acts as a T cell costimulatory molecule, enhancing anti-CD3 induced proliferation and enhancing IL-4 production in T cells induced with anti-CD3.

EXAMPLE 8

This example shows that the DCAL-1-His soluble receptor enhances the stimulatory capacity of DCs in an allogenic mixed lymphocyte reaction.

Methods: Mixed lymphocyte reactions (MLRs) were set up by culturing different concentrations (1,500-50,000/well) of gamma-irradiated monocyte derived dendritic cells (MD-DCs) using (3,000 rad of $^{137}Cs$) with 10,000/well of CD4+ CD4RA+ T cells. These cells were co-cultured in 96 well, round bottom microtiter plates in a final volume of 2000 for 3 days with soluble DCAL-1-His or DC-SIGN-His (0, 5.0 and 10.0 µg/ml), made as described in Example 3. T cell proliferation was assessed on day 4 after the addition of 1 µCi/well of [$^3$H]thymidine (Amersham, Arlington Heights, Ill.) for the final 9 hours. [$^3$H]thymidine incorporation was measured by liquid scintillation counting. All determinations were performed in triplicate and measured as the mean counts per minute ±SD.

Figure 6:
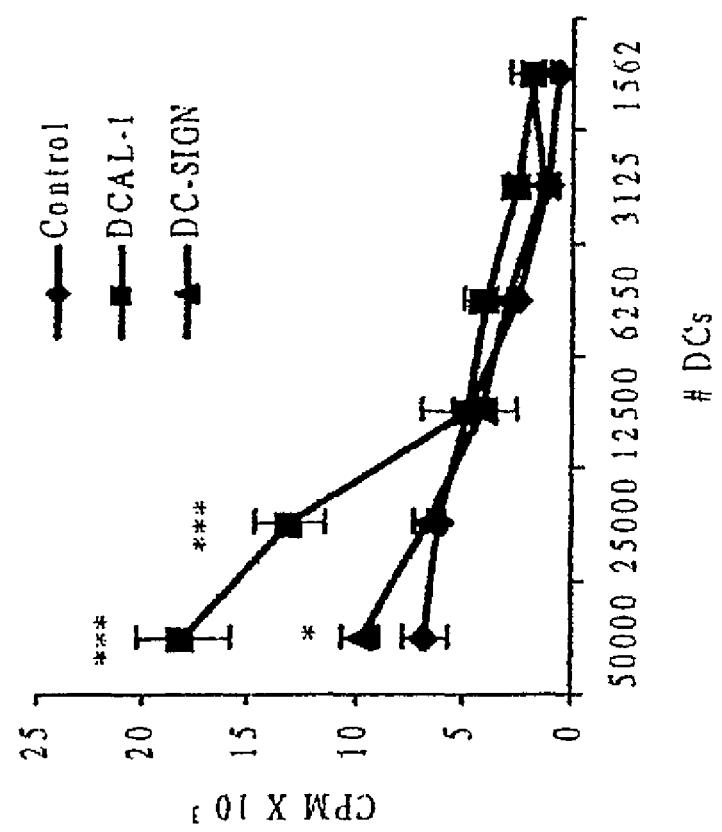
FIG. 6 graphically illustrates that the DCAL-1 soluble receptor enhances the stimulatory capacity of DCs in an allogenic mixed lymphocyte reaction (MLR), as described in Example 8.

Results: As shown in FIG. 6, DCAL-1-His enhanced the stimulatory capacity of monocyte-derived DCs in an allogenic MLR. In a dose-response experiment where 0, 5, 10 and 25 µg/ml of soluble DCAL-1-His or DC-SIGN-His was included in a MLR, maximum proliferation was observed with the 10 µg/ml dose of DCAL-1-His (data not shown).

EXAMPLE 9

This example presents data which demonstrates that stimulation of immature DCs with the anti-DCAL-1 mAb UW50 induces immature DCs to mature.

Preparation of Cells: CD14+ human monocytes were purified by immunomagnetic positive selection (anti-CD14 mAb-conjugated microbeads by Miltenyi Biotech) from leukophoresed peripheral blood from volunteer donors. Purified monocytes were then cultured at $3×10^6$/ml for 6 days in 10% FCS, RPMI, 2-ME (50 µm), GM-CSF (100 ng/ml, Amgen, Seattle, Wash.) and IL-4 (30 ng/ml, Biosource). The cells were fed at day 2 and 4 by replacing half the medium containing the full amount of cytokines. After 6 days in culture, monocytes (CD14+, CD1a low) were phenotyped by FACS to determine if they had differentiated into immature dendritic cells (CD14−, CD1a high and CD83low).

The cell concentration of immature dendritic cells was adjusted to $1×10^6$/ml, and cells were seeded at 3.5 ml per well in a 12 well plate. The cells were then exposed to various stimuli and analyzed by Western Blot, FACS and ELISA.

Figure 7A:
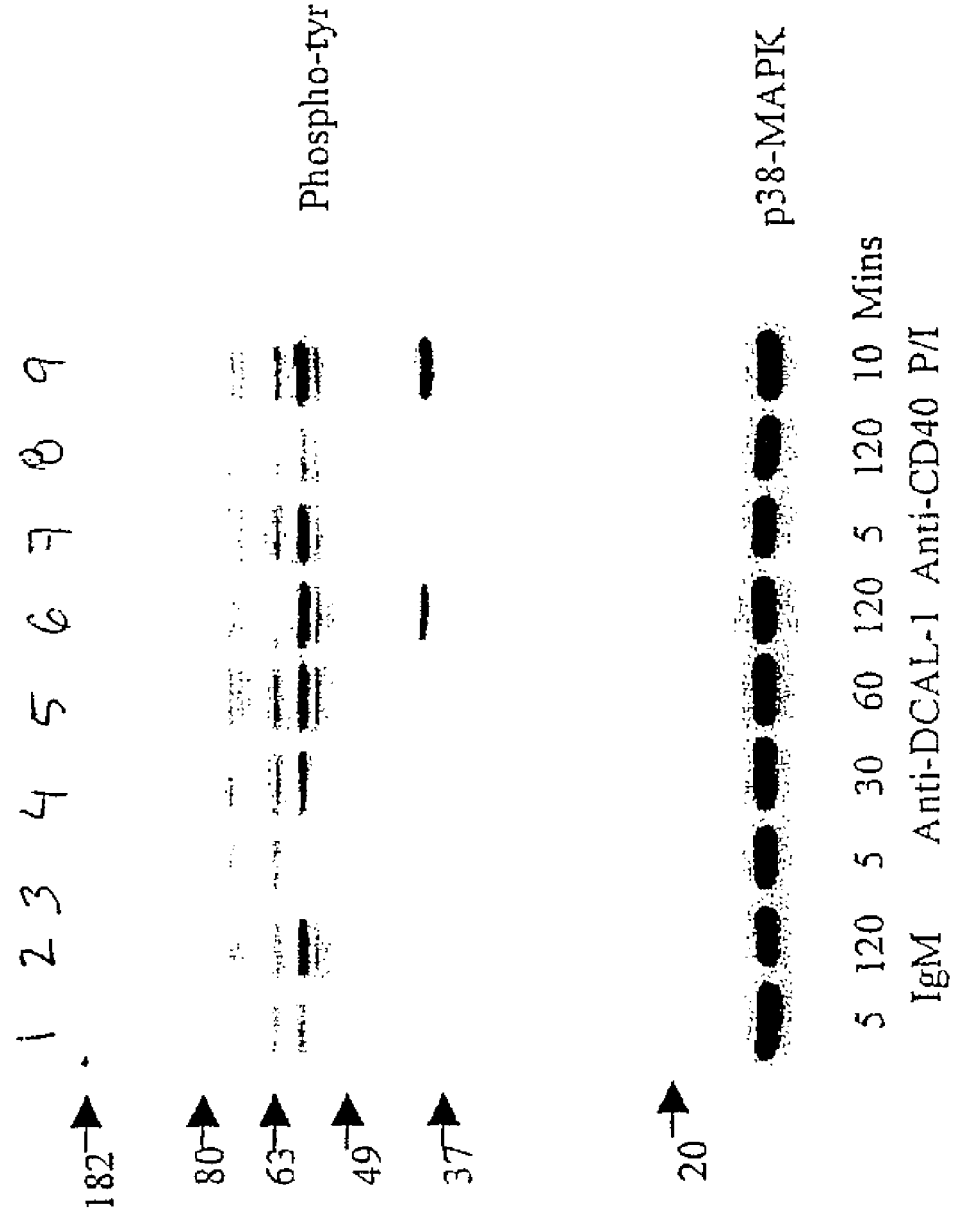
FIG. 7A demonstrates that ligation of DCAL-1 with anti-DCAL-1 Ab induces tyrosine phosphorylation of downstream signaling molecules in DC.
Figure 7B:
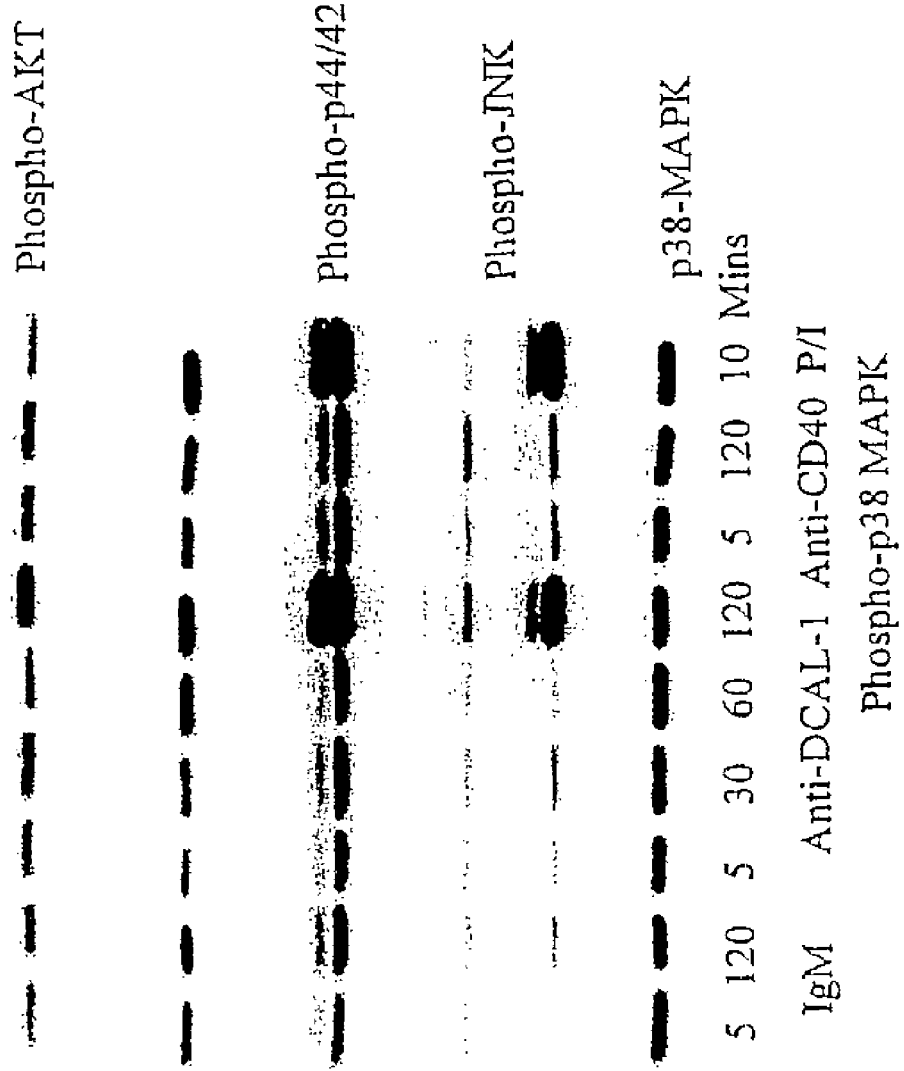
FIG. 7B demonstrates that ligation of DCAL-1 with an anti-DCAL-1 Ab (UW50) increases Phospho-p44/42 MAPK, Phospho-JNK and Phospho-AKT levels, but not Phospho-p38 MAPK.

Western Blot Methods: Immature DCs were prepared as described above. The results shown in FIGS. 7A and 7B are representative of two experiments performed with DCs obtained from different donors. Immature DCs were plated as described above, with the addition of the anti-DCAL-1 mAb (UW50) at 100 µg/ml per well or anti-CD40 mAb(G28-5). A time course was carried out with harvest at 5 minutes, 30 minutes, 1 hour, 2 hours, 4 hours, 6 hours and 24 hours. For a positive control, cells were incubated with PMA (50 ng/ml) and Ionomycin (1 ng/ml) for 10 minutes. For a negative control, cells were incubated with IgM isotype control for 5 minutes and 2 hours. Cells were lysed in 1% Triton X-100 lysis buffer for 15 minutes on ice and cell membranes were spun down. Protein lysates (30 µg) were electrophoresed on 10% SDS-PAGE gels, transferred to nitrocellulose membranes (Scheicher & Schuell, Dassel, Germany), and blotted with phospho-ERK Abs (New England Biolabs), followed by anti-rabbit HRP (Santa Cruz Biotechnology, Santa Cruz, Calif.) and detected by chemiluminescence (ECL, Amersham, Aylesbury, United Kingdom). Antibodies to total p38 MAP Kinase (rabbit polyclonal, Santa Cruz cat. # sc 535) were used as loading controls. The following proteins were analyzed: phospho-Akt (rabbit polyclonal, Cell Signaling cat. #9271), phospho-Tyrosine (mouse monoclonal Ab 4G10, gift from Dr. Michael Gold, Univ. of British Columbia), phospho-p38 MAP Kinase (rabbit polyclonal, Cell Signaling, Cat. #9211), phospho-ERK (rabbit polyclonal, Cell Signaling cat. #9101) and phospho-JNK (rabbit polyclonal, Cell Signaling, cat. #9251).

Western Blot Results: As shown in FIG. 7A, stimulation of immature DCs with anti-DCAL-1 mAb induces tyrosine phosphorylation (lanes 4-6) to levels similar to the positive control (lane 9). As shown in FIG. 7B, the Phospho-p42/44 MAPK, Phospho-AKT and Phospho-JNK levels increased after stimulation with anti-DCAL-1 mAb (lane 6) to levels similar to the P/I positive control (lane 9), whereas stimulation with anti-CD40 mAb (lane 8) resulted in lower levels. Total p-38 MAPK levels were used as a control for equal protein loading.

The phosphorylated forms of AKT/PKB, ERK and MAP38 kinases are known to be an indication that the kinases have been activated. See for example, Andjelkovic, M. et al., *Mol. Cell. Biol.* 19(7):5061-72 (1999); Craxton, A., et al., *J. Biol. Chem.* 22; 274 (43):30644-50 (1999); Gold, M. R., et al., *J. Immunol.* 163(4):1894-1905 (1999); Jiang, A., et al., *J. Exp. Med.* 188(7):1297-1306 (1998) and Tazzari, P. L., et al., *J. Cell Biochem.* 86(4):704-715 (2002).

Further, the activation of AKT/PKB and ERK suggests that DCAL-1 ligation may lead to longer survival of DCs because these kinases have been shown to be involved in promoting cell survival. For AKT/PKB pathways, see, for example, Cantrell, D., *Seminars in Immunol.* 14(1):19-26 (2002); Cantley, L. C., *Science* 296(5573):1655-1657 (2002); Kane, L. P., et al., *Immunol. Rev.* 192:7-20 (2003); Plas, D. R., et al., *Nat. Immunol.* 3(6):515-521 (2002). For the ERK pathway, see Xaus, J., et al., *Immunobiology* 204(5):543-550 (2001); Grewal, S. S., et al., *Neurobiol.* 9(5):544-553 (1999); Schwartz, M. A. et al., *J. Cell Sci.* 114(14):2553-2560 (2001) and Herrera, R., et al., *Trends Mol. Med.* 8(4):527-31 (2002). Therefore, the results indicate that DCAL-1 ligation may lead to longer survival of DC's, thus resulting in the ability to sustain an immune response for a longer period of time.

FACS Methods: The cells were prepared as described above and the following stimuli were added: anti-DCAL-1 mAb (UW50) (1 µg/ml, 5 µg/ml and 10 µg/ml). Cells were incubated with IgM for 5 min as a negative control. For a positive control, cells were incubated for 5 min with anti-CD40 (G28-5 10 µg/ml), and LPS (*E. coli*, Sigma 1 µg/ml. The cells were incubated at 5% $CO_2$, 37° C. for 48 hours.

After 48 hours, supernatants were removed and frozen at −20° C. for cytokine analysis. The cells were then removed by gently scraping and stained with the following fluorochrome conjugated mAbs: CD1a, CD80, CD83, CD86, HLA-DR and CD40. The FACScan was gated on live cells, 10,000 events were acquired and the data was analyzed by Cellquest software.

FACScan Results: The results are shown below in TABLE 6. Ligation of DCAL-1 on immature DCs downregulates cell surface expression of CD1a consistent with an induction of DC maturation. Ligation of DCAL-1 on immature DCs also upregulates cell surface expression of HLA-DR, again suggesting it is inducing immature DCs to mature. As further shown in TABLE 6, ligation of DCAL-1 on immature DCs does not appear to significantly affect cell surface expression of CD83, CD80, CD86 and CD40. Thus, DCAL-1 ligation alone is not sufficient to drive immature DCs to become typical mature DCs.

TABLE 6

DCAL-1 dependent regulation of cell surface activation markers

| Cell Surface Marker | Isotype Control (1 µg/ml) | Isotype Control (10 µg/ml) | Isotype Control (100 µg/ml) | Anti-DCAL-1 (1 µg/ml) | Anti-DCAL-1 (10 µg/ml) | Anti-DCAL-1 (100 µg/ml) |
|---|---|---|---|---|---|---|
| CD1A | 2059 | 1852 | 1770 | 1619 | 1399 | 1362 |
| CD83 | 33.03 | 31.73 | 31.06 | 24.29 | 30.56 | 30.22 |
| HLA-DR | 619.53 | 608.74 | 828.11 | 843.53 | 739.97 | 737.71 |
| CD80 | 176 | 133 | 141 | 129 | 166 | 147 |
| CD86 | 592 | 647 | 632 | 611 | 660 | 640 |
| CD40 | 192 | 192 | 186 | 189 | 166 | 176 |

Cytokine Detection Methods: Cytokine analysis was carried out by ELISA as previously described in Example 7.

Cytokine Results: The results are shown below in TABLE 7. The results are presented from two different donors, with anti-DCAL-1 mAb UW50 added at 1 µg/ml, 10 µg/ml and 100 µg/ml. As shown in TABLE 7, the UW50 mAb results in a dose-dependant increase in IL-6 secretion. Thus, DCAL-1 ligation selectively activates expression of some but not all DC-associated cytokines, and may promote a cell maturation program involving IL-6.

These results demonstrate that while DCAL-1 ligation promotes DC maturation, the anti-DCAL-1 mAb stimulated DCs do not appear to be fully matured as compared to DCs stimulated with anti-CD40 mAb or LPS which are known to induce DC maturation. See Lutz, M. B., Trends Immunol. 23(9): 445-449 (2002). Therefore, DCAL-1 ligation may promote DC maturation to a semi-mature state which may be important for producing a tolerizing response. See Bouchon et al., J. Exp. Med. 194(8): 1111-1122 (2001).

EXAMPLE 10

This example shows that DCAL-1 cell surface expression is up-regulated by both IL-4 and IL-13, however, this upregulation is inhibited in the presence of GM-CSF.

Methods: CD14+ monocytes were obtained as described in Example 9. Purified monocytes were then cultured at $3\times10^6$/ml for 6 days in 10% FCS, RPMI, 2-ME (50 µm) with the following cytokines: IL-4 (30 ng/ml) alone, GM-CSF (100 ng/ml) alone, IL-13 (30 ng/ml) alone, IL-4 plus GM-CSF and IL-13 plus GM-CSF. The cells were fed at day 2 and 4 by replacing half the medium containing the full amount of cytokines. After 6 days in culture, monocytes (CD14+, CD1a low) were phenotyped by FACS to determine if they had differentiated into immature dendritic cells (CD14−, CD1a high and CD83low). On day 6, cells were incubated with the DCAL-1 mAb (UW50) followed by rat anti-mouse IgM-FITC and DCAL-1 protein expression was determined by flow cytometry on a FACSan analyzer (BD Biosciences, Mountain View, Calif.).

Results: An induction of DCAL-1 expression was observed in the presence of IL-4 (71.73% cells bound, M.F.I. 1116.45) and IL-13 (84.73% cells bound, M.F.I. 1652.94) compared to the media only control (60.35% cells bound, M.F.I. 411.12). The upregulation of DCAL-1 observed with IL-4 and IL-13 was inhibited in the presence of GM-CSF. GM-CSF alone (45.60% cells bound, M.F.I. 188), GM-CSF plus IL-4 (35.5% cells bound, M.F.I. 258.97), GM-CSF plus IL-13 (78.1% cells bound, M.F.I. 322.45). As shown in Example 7, the DCAL-1-His soluble receptor increases T cell secretion of IL-4. Therefore, DCAL-1 may be involved in a positive feedback loop that modulates the development of Th2 responses.

While the preferred embodiment of the invention has been illustrated and described, it will be appreciated that various changes can be made therein without departing from the spirit and scope of the invention.

TABLE 7

DCAL-1 dependent induction of cytokine secretion

| | Isotype Control (1 µg/ml) | Isotype Control (10 µg/ml) | Isotype Control (100 µg/ml) | Anti-DCAL-1 (1 µg/ml) | Anti-DCAL-1 (10 µg/ml) | Anti-DCAL-1 (100 µg/ml) |
|---|---|---|---|---|---|---|
| IL-6 | 119.33 (±19.43) | 285 (±29.08) | 263.5 (±21.02) | 368.25 (±14.11) | 420.75 (±16.65) | 506.75 (±65.65) |
| IL-8 | 1345.67 (±674.46) | 1556.67 (±323.67) | 1129.33 (±176.14) | 1536.33 (±492.67) | 2070 (±554.67) | 1906 (±524.9) |
| IL-10 | 37.25 (±8.77) | 37 (±7.07) | 40 (±6.98) | 42.75 (±8.06) | 43.75 (±11.27) | 43.25 (±12.69) |
| IL-12 | 485 (±297.54) | 548 (±170.97) | 465 (±167.03) | 354 (±289.28) | 442 (±409.77) | 423 (±430.03) |

The embodiments of the invention in which an exclusive property or privilege is claimed are defined as follows:

1. A method of stimulating an immune response in a mammalian subject comprising the step of administering to the subject an amount of an anti-DCAL-1 antibody, or an antigen binding fragment thereof, sufficient to stimulate an immune response in the subject, wherein the anti-DCAL-1 antibody or antigen binding fragment thereof binds to a DCAL-1 polypeptide comprising SEQ ID NO:13, and wherein the anti-DCAL-1 antibody is UW50 produced by the hybridoma cell line designated ATCC Deposit No. PTA-9866.

2. The method of claim 1, wherein the anti-DCAL-1 antibody, or antigen binding fragment thereof, is administered in combination with an antigen.

3. The method of claim 2, wherein the anti-DCAL-1 antibody, or antigen binding fragment thereof, is conjugated to the antigen.

4. The method of claim 2, wherein the antigen is an antigenic peptide.

5. The method of claim 2, wherein the antigen is a tumor associated antigen.

6. The method of claim 2, wherein the antigen is derived from a pathogen.

7. The method of claim 1, wherein the antibody, or antigen binding fragment thereof, is conjugated to an imaging moiety.

8. The method of claim 1, wherein the antibody, or antigen binding fragment thereof, is conjugated to a cytotoxic moiety.

9. The method of claim 1, wherein the mammalian subject is suffering from a disease or condition selected from the group consisting of cancer, viral infection, fungal infection, bacterial infection, parasitic infection and autoimmune disease.

10. The method of claim 1, wherein the mammalian subject is at risk for a disease or condition selected from the group consisting of cancer, viral infection, fungal infection, bacterial infection, parasitic infection and autoimmune disease.

11. A method for targeting a therapeutic agent to a dendritic cell in an animal comprising the step of introducing into said animal an anti-DCAL-1 antibody or an antigen binding fragment thereof conjugated to said therapeutic agent, wherein the anti-DCAL-1 antibody or antigen binding fragment thereof binds to a DCAL-1 polypeptide comprising SEQ ID NO:13, wherein the antibody is UW50 produced by the hybridoma cell line designated ATCC Deposit No. PTA-9866.

12. The method of claim 11, wherein said therapeutic agent is an antigenic peptide.

13. The method of claim 12, wherein said antigenic peptide is a tumor associated antigen.

* * * * *

UNITED STATES PATENT AND TRADEMARK OFFICE
CERTIFICATE OF CORRECTION

| | | |
|---|---|---|
| PATENT NO. | : 8,246,959 B1 | Page 1 of 1 |
| APPLICATION NO. | : 11/620582 | |
| DATED | : August 21, 2012 | |
| INVENTOR(S) | : Clark et al. | |

It is certified that error appears in the above-identified patent and that said Letters Patent is hereby corrected as shown below:

In the Specification

| COLUMN | LINE | |
|---|---|---|
| 1 | 15 | after "funded" delete ", in part," |

Signed and Sealed this

Thirteenth Day of May, 2014

Michelle K. Lee
*Deputy Director of the United States Patent and Trademark Office*

SEQUENCE LISTING

<160> NUMBER OF SEQ ID NOS: 15

<210> SEQ ID NO 1
<211> LENGTH: 672
<212> TYPE: DNA
<213> ORGANISM: Homo sapiens
<220> FEATURE:
<221> NAME/KEY: CDS
<222> LOCATION: (1)..(672)

<400> SEQUENCE: 1

| | | | | | | | | | | | | | | | | |
|---|---|---|---|---|---|---|---|---|---|---|---|---|---|---|---|---|
| atg | gtt | agt | aat | ttc | ttc | cat | gtc | ata | caa | gta | ttc | gag | aaa | tct | gct | 48 |
| Met | Val | Ser | Asn | Phe | Phe | His | Val | Ile | Gln | Val | Phe | Glu | Lys | Ser | Ala | |
| 1 | | | | 5 | | | | | 10 | | | | | 15 | | |
| acc | ttg | att | agt | aag | act | gaa | cac | att | ggt | ttt | gtc | att | tat | tca | tgg | 96 |
| Thr | Leu | Ile | Ser | Lys | Thr | Glu | His | Ile | Gly | Phe | Val | Ile | Tyr | Ser | Trp | |
| | | | 20 | | | | | 25 | | | | | 30 | | | |
| agg | aag | tcc | acc | acc | cac | ttg | ggg | agc | aga | agg | aaa | ttt | gcc | atc | tca | 144 |
| Arg | Lys | Ser | Thr | Thr | His | Leu | Gly | Ser | Arg | Arg | Lys | Phe | Ala | Ile | Ser | |
| | | 35 | | | | | 40 | | | | | 45 | | | | |
| att | tac | tta | tca | gaa | gtt | tct | ttg | cag | aaa | tat | gat | tgt | ccc | ttc | agt | 192 |
| Ile | Tyr | Leu | Ser | Glu | Val | Ser | Leu | Gln | Lys | Tyr | Asp | Cys | Pro | Phe | Ser | |
| | 50 | | | | | 55 | | | | | 60 | | | | | |
| ggg | aca | tca | ttt | gtg | gtc | ttc | tct | ctc | ttt | ttg | atc | tgt | gca | atg | gct | 240 |
| Gly | Thr | Ser | Phe | Val | Val | Phe | Ser | Leu | Phe | Leu | Ile | Cys | Ala | Met | Ala | |
| 65 | | | | | 70 | | | | | 75 | | | | | 80 | |
| gga | gat | gta | gtc | tac | gct | gac | atc | aaa | act | gtt | cgg | act | tcc | ccg | tta | 288 |
| Gly | Asp | Val | Val | Tyr | Ala | Asp | Ile | Lys | Thr | Val | Arg | Thr | Ser | Pro | Leu | |
| | | | | 85 | | | | | 90 | | | | | 95 | | |
| gaa | ctc | gcg | ttt | cca | ctt | cag | aga | tct | gac | ttc | aat | tct | ttt | aat | ttt | 336 |
| Glu | Leu | Ala | Phe | Pro | Leu | Gln | Arg | Ser | Asp | Phe | Asn | Ser | Phe | Asn | Phe | |
| | | | 100 | | | | | 105 | | | | | 110 | | | |
| ttt | tca | aat | gta | ccc | tgg | aac | aaa | gca | cat | act | ttt | ttc | aaa | gaa | agc | 384 |
| Phe | Ser | Asn | Val | Pro | Trp | Asn | Lys | Ala | His | Thr | Phe | Phe | Lys | Glu | Ser | |
| | | 115 | | | | | 120 | | | | | 125 | | | | |
| tta | gca | cat | aat | ata | acc | aaa | ttt | gag | acc | ctt | caa | tta | gta | tac | att | 432 |
| Leu | Ala | His | Asn | Ile | Thr | Lys | Phe | Glu | Thr | Leu | Gln | Leu | Val | Tyr | Ile | |
| | 130 | | | | | 135 | | | | | 140 | | | | | |
| att | agg | ata | cag | ttt | tac | att | gat | ttt | aat | tgc | tta | tct | tcc | ttt | ctt | 480 |
| Ile | Arg | Ile | Gln | Phe | Tyr | Ile | Asp | Phe | Asn | Cys | Leu | Ser | Ser | Phe | Leu | |
| 145 | | | | | 150 | | | | | 155 | | | | | 160 | |
| cca | gtt | tct | ttc | aac | ttt | tct | act | gtc | cat | aaa | tca | tgt | cct | gcc | aaa | 528 |
| Pro | Val | Ser | Phe | Asn | Phe | Ser | Thr | Val | His | Lys | Ser | Cys | Pro | Ala | Lys | |
| | | | | 165 | | | | | 170 | | | | | 175 | | |
| gac | tgg | aag | gtg | cat | aag | gga | aaa | tgt | tac | tgg | att | gct | gaa | act | aag | 576 |
| Asp | Trp | Lys | Val | His | Lys | Gly | Lys | Cys | Tyr | Trp | Ile | Ala | Glu | Thr | Lys | |
| | | | 180 | | | | | 185 | | | | | 190 | | | |
| aaa | tct | tgg | aac | aaa | agt | caa | aat | gac | tgt | gcc | ata | aac | aat | tca | tat | 624 |
| Lys | Ser | Trp | Asn | Lys | Ser | Gln | Asn | Asp | Cys | Ala | Ile | Asn | Asn | Ser | Tyr | |
| | | 195 | | | | | 200 | | | | | 205 | | | | |
| ctc | atg | gtg | att | caa | gac | att | act | gct | atg | gtg | aga | ttt | aac | att | tag | 672 |
| Leu | Met | Val | Ile | Gln | Asp | Ile | Thr | Ala | Met | Val | Arg | Phe | Asn | Ile | | |
| | 210 | | | | | 215 | | | | | 220 | | | | | |

<210> SEQ ID NO 2
<211> LENGTH: 223
<212> TYPE: PRT
<213> ORGANISM: Homo sapiens

<400> SEQUENCE: 2

```
Met Val Ser Asn Phe Phe His Val Ile Gln Val Phe Glu Lys Ser Ala
1               5                   10                  15

Thr Leu Ile Ser Lys Thr Glu His Ile Gly Phe Val Ile Tyr Ser Trp
            20                  25                  30

Arg Lys Ser Thr Thr His Leu Gly Ser Arg Arg Lys Phe Ala Ile Ser
                35                  40                  45

Ile Tyr Leu Ser Glu Val Ser Leu Gln Lys Tyr Asp Cys Pro Phe Ser
        50                  55                  60

Gly Thr Ser Phe Val Val Phe Ser Leu Phe Leu Ile Cys Ala Met Ala
65                  70                  75                  80

Gly Asp Val Val Tyr Ala Asp Ile Lys Thr Val Arg Thr Ser Pro Leu
                85                  90                  95

Glu Leu Ala Phe Pro Leu Gln Arg Ser Asp Phe Asn Ser Phe Asn Phe
                100                 105                 110

Phe Ser Asn Val Pro Trp Asn Lys Ala His Thr Phe Lys Glu Ser
            115                 120                 125

Leu Ala His Asn Ile Thr Lys Phe Glu Thr Leu Gln Leu Val Tyr Ile
        130                 135                 140

Ile Arg Ile Gln Phe Tyr Ile Asp Phe Asn Cys Leu Ser Ser Phe Leu
145                 150                 155                 160

Pro Val Ser Phe Asn Phe Ser Thr Val His Lys Ser Cys Pro Ala Lys
                165                 170                 175

Asp Trp Lys Val His Lys Gly Lys Cys Tyr Trp Ile Ala Glu Thr Lys
                180                 185                 190

Lys Ser Trp Asn Lys Ser Gln Asn Asp Cys Ala Ile Asn Asn Ser Tyr
                195                 200                 205

Leu Met Val Ile Gln Asp Ile Thr Ala Met Val Arg Phe Asn Ile
210                 215                 220

<210> SEQ ID NO 3
<211> LENGTH: 504
<212> TYPE: DNA
<213> ORGANISM: Homo sapiens
<220> FEATURE:
<221> NAME/KEY: CDS
<222> LOCATION: (1)..(504)

<400> SEQUENCE: 3 atg gtt agt aat ttc ttc cat gtc ata caa gta ttc gag aaa tct gct    48
Met Val Ser Asn Phe Phe His Val Ile Gln Val Phe Glu Lys Ser Ala
1               5                   10                  15 acc ttg att agt aag act gaa cac att ggt ttt gtc att tat tca tgg    96
Thr Leu Ile Ser Lys Thr Glu His Ile Gly Phe Val Ile Tyr Ser Trp
            20                  25                  30 agg aag tcc acc acc cac ttg ggg agc aga agg aaa ttt gcc atc tca   144
Arg Lys Ser Thr Thr His Leu Gly Ser Arg Arg Lys Phe Ala Ile Ser
                35                  40                  45 att tac tta tca gaa gtt tct ttg cag aaa tat gat tgt ccc ttc agt   192
Ile Tyr Leu Ser Glu Val Ser Leu Gln Lys Tyr Asp Cys Pro Phe Ser
        50                  55                  60 ggg aca tca ttt gtg gtc ttc tct ctc ttt ttg atc tgt gca atg gct   240
Gly Thr Ser Phe Val Val Phe Ser Leu Phe Leu Ile Cys Ala Met Ala
65                  70                  75                  80 gga gat gta gtc tac gct gac atc aaa act gtt cgg act tcc ccg tta   288
Gly Asp Val Val Tyr Ala Asp Ile Lys Thr Val Arg Thr Ser Pro Leu
                85                  90                  95 gaa ctc gcg ttt cca ctt cag aga tct gtt tct ttc aac ttt tct act   336
Glu Leu Ala Phe Pro Leu Gln Arg Ser Val Ser Phe Asn Phe Ser Thr
                100                 105                 110
```

-continued

```
gtc cat aaa tca tgt cct gcc aaa gac tgg aag gtg cat aag gga aaa      384
Val His Lys Ser Cys Pro Ala Lys Asp Trp Lys Val His Lys Gly Lys
        115                 120                 125 tgt tac tgg att gct gaa act aag aaa tct tgg aac aaa agt caa aat      432
Cys Tyr Trp Ile Ala Glu Thr Lys Lys Ser Trp Asn Lys Ser Gln Asn
130                 135                 140 gac tgt gcc ata aac aat tca tat ctc atg gtg att caa gac att act      480
Asp Cys Ala Ile Asn Asn Ser Tyr Leu Met Val Ile Gln Asp Ile Thr
145                 150                 155                 160 gct atg gtg aga ttt aac att tag                                      504
Ala Met Val Arg Phe Asn Ile
                165

<210> SEQ ID NO 4
<211> LENGTH: 167
<212> TYPE: PRT
<213> ORGANISM: Homo sapiens

<400> SEQUENCE: 4

Met Val Ser Asn Phe Phe His Val Ile Gln Val Phe Glu Lys Ser Ala
1               5                   10                  15

Thr Leu Ile Ser Lys Thr Glu His Ile Gly Phe Val Ile Tyr Ser Trp
            20                  25                  30

Arg Lys Ser Thr Thr His Leu Gly Ser Arg Lys Phe Ala Ile Ser
        35                  40                  45

Ile Tyr Leu Ser Glu Val Ser Leu Gln Lys Tyr Asp Cys Pro Phe Ser
    50                  55                  60

Gly Thr Ser Phe Val Val Phe Ser Leu Phe Leu Ile Cys Ala Met Ala
65                  70                  75                  80

Gly Asp Val Val Tyr Ala Asp Ile Lys Thr Val Arg Thr Ser Pro Leu
                85                  90                  95

Glu Leu Ala Phe Pro Leu Gln Arg Ser Val Ser Phe Asn Phe Ser Thr
            100                 105                 110

Val His Lys Ser Cys Pro Ala Lys Asp Trp Lys Val His Lys Gly Lys
        115                 120                 125

Cys Tyr Trp Ile Ala Glu Thr Lys Lys Ser Trp Asn Lys Ser Gln Asn
    130                 135                 140

Asp Cys Ala Ile Asn Asn Ser Tyr Leu Met Val Ile Gln Asp Ile Thr
145                 150                 155                 160

Ala Met Val Arg Phe Asn Ile
                165

<210> SEQ ID NO 5
<211> LENGTH: 22
<212> TYPE: DNA
<213> ORGANISM: Artificial
<220> FEATURE:
<223> OTHER INFORMATION: PCR primers

<400> SEQUENCE: 5
aaaacgagaa cctactgtat gg                                             22

<210> SEQ ID NO 6
<211> LENGTH: 25
<212> TYPE: DNA
<213> ORGANISM: Artificial
<220> FEATURE:
<223> OTHER INFORMATION: PCR primers

<400> SEQUENCE: 6
```

```
ctaaatgtta aatctcacca tagca                                          25

<210> SEQ ID NO 7
<211> LENGTH: 28
<212> TYPE: DNA
<213> ORGANISM: Artificial
<220> FEATURE:
<223> OTHER INFORMATION: PCR primers

<400> SEQUENCE: 7
gtgcaatggc tggagatgta gtctacgc                                       28

<210> SEQ ID NO 8
<211> LENGTH: 26
<212> TYPE: DNA
<213> ORGANISM: Artificial
<220> FEATURE:
<223> OTHER INFORMATION: PCR primers

<400> SEQUENCE: 8
tcactgccag tgtgggggat gctgtc                                         26

<210> SEQ ID NO 9
<211> LENGTH: 20
<212> TYPE: DNA
<213> ORGANISM: Artificial
<220> FEATURE:
<223> OTHER INFORMATION: PCR primers

<400> SEQUENCE: 9
accacagtcc atgccatcac                                                20

<210> SEQ ID NO 10
<211> LENGTH: 20
<212> TYPE: DNA
<213> ORGANISM: Artificial
<220> FEATURE:
<223> OTHER INFORMATION: PCR primers

<400> SEQUENCE: 10
tccaccaccc tgttgctgta                                                20

<210> SEQ ID NO 11
<211> LENGTH: 37
<212> TYPE: DNA
<213> ORGANISM: Artificial
<220> FEATURE:
<223> OTHER INFORMATION: PCR primers

<400> SEQUENCE: 11
gttgttggat ccaatcaaaa ctgttcggac ttccccg                             37

<210> SEQ ID NO 12
<211> LENGTH: 35
<212> TYPE: DNA
<213> ORGANISM: Artificial
<220> FEATURE:
<223> OTHER INFORMATION: PCR primers

<400> SEQUENCE: 12
cgcaagcttt gttcattcaa ctaatatttg tatag                               35

<210> SEQ ID NO 13
<211> LENGTH: 42
<212> TYPE: PRT
<213> ORGANISM: artificial
<220> FEATURE:
```

```
<223> OTHER INFORMATION: PCR primers

<400> SEQUENCE: 13

Cys Pro Ala Lys Asp Trp Lys Val His Lys Gly Lys Cys Tyr Trp Ile
1               5                   10                  15

Ala Glu Thr Lys Lys Ser Trp Asn Lys Ser Gln Asn Asp Cys Ala Ile
            20                  25                  30

Asn Asn Ser Tyr Leu Met Val Ile Gln Asp
        35                  40

<210> SEQ ID NO 14
<211> LENGTH: 115
<212> TYPE: PRT
<213> ORGANISM: Homo sapiens

<400> SEQUENCE: 14

Lys Thr Val Arg Thr Ser Pro Leu Glu Leu Ala Phe Pro Leu Gln Arg
1               5                   10                  15

Ser Asp Phe Asn Ser Phe Asn Phe Ser Asn Val Pro Trp Asn Lys
            20                  25                  30

Ala His Thr Phe Phe Lys Glu Ser Leu Ala His Asn Ile Thr Lys Phe
            35                  40                  45

Glu Thr Leu Gln Leu Val Tyr Ile Ile Arg Ile Gln Phe Tyr Ile Asp
        50                  55                  60

Phe Asn Cys Leu Ser Ser Phe Leu Pro Val Ser Phe Asn Phe Ser Thr
65                  70                  75                  80

Val His Lys Ser Cys Pro Ala Lys Asp Trp Lys Val His Lys Gly Lys
                85                  90                  95

Cys Tyr Trp Ile Ala Glu Thr Lys Lys Ser Trp Asn Lys Ser Gln Asn
            100                 105                 110

Asp Cys Ala
        115

<210> SEQ ID NO 15
<211> LENGTH: 83
<212> TYPE: PRT
<213> ORGANISM: Homo sapiens

<400> SEQUENCE: 15

Tyr Ala Asp Ile Lys Thr Val Arg Thr Ser Pro Leu Glu Leu Ala Phe
1               5                   10                  15

Pro Leu Gln Arg Ser Val Ser Phe Asn Phe Ser Thr Val His Lys Ser
            20                  25                  30

Cys Pro Ala Lys Asp Trp Lys Val His Lys Gly Lys Cys Tyr Trp Ile
            35                  40                  45

Ala Glu Thr Lys Lys Ser Trp Asn Lys Ser Gln Asn Asp Cys Ala Ile
        50                  55                  60

Asn Asn Ser Tyr Leu Met Val Ile Gln Asp Ile Thr Ala Met Val Arg
65                  70                  75                  80

Phe Asn Ile
```